(12) United States Patent
Meada et al.

(10) Patent No.: US 7,850,636 B2
(45) Date of Patent: Dec. 14, 2010

(54) CLOSED-TYPE BLOOD RESERVOIR AND EXTRACORPOREAL BLOOD CIRCULATION APPARATUS USING THE SAME

(75) Inventors: Hiroyuki Meada, Hiroshima (JP); Shigeki Kawarabata, Hiroshima (JP)

(73) Assignee: JMS Co., Ltd., Hiroshima (JP)

( * ) Notice: Subject to any disclaimer, the term of this patent is extended or adjusted under 35 U.S.C. 154(b) by 445 days.

(21) Appl. No.: 11/992,839

(22) PCT Filed: Oct. 3, 2006

(86) PCT No.: PCT/JP2006/319784

§ 371 (c)(1),
(2), (4) Date: Mar. 31, 2008

(87) PCT Pub. No.: WO2007/040223

PCT Pub. Date: Apr. 12, 2007

(65) Prior Publication Data

US 2009/0062716 A1 Mar. 5, 2009

(30) Foreign Application Priority Data

Oct. 3, 2005 (JP) ............................ 2005-290210
Oct. 4, 2005 (JP) ............................ 2005-291204
Oct. 4, 2005 (JP) ............................ 2005-291206

(51) Int. Cl.
*A61M 37/00* (2006.01)
(52) U.S. Cl. .................... 604/6.15; 604/6.09
(58) Field of Classification Search ............... 604/6.15, 604/6.09, 403, 6.11
See application file for complete search history.

(56) References Cited

U.S. PATENT DOCUMENTS 4,630,597 A 12/1986 Kantrowitz et al.

(Continued)

FOREIGN PATENT DOCUMENTS

EP 0 987 035 3/2000

(Continued)

*Primary Examiner*—Leslie R Deak
(74) *Attorney, Agent, or Firm*—Hamre, Schumann, Mueller & Larson, P.C.

(57) ABSTRACT

An example of the closed-type blood reservoir of the invention is furnished with an outer shell in which a space is formed within its interior, a flexible septum that is interposed between a blood storage chamber shell and a volume adjustment chamber shell and that divides the space into a blood storage chamber for storing blood and a volume adjustment chamber for storing volume adjustment liquid, a blood inlet port, a blood outlet port, and a blood storage chamber air discharge port that are provided in the blood storage chamber shell such that they are in communication with the blood storage chamber, and a volume adjustment liquid port that is provided in the volume adjustment chamber shell such that it is in communication with the volume adjustment chamber, for injecting and ejecting the volume adjustment liquid into and away from the volume adjustment chamber, wherein the blood inlet port and the blood outlet port each are provided tangentially to the inner surface of the blood storage chamber shell such that blood that flows into the blood storage chamber from the blood inlet port can swirl along the inner surface of the blood storage chamber shell, and wherein the closed-type blood reservoir has a first blood flow route, provided in the blood storage chamber, that is formed by an outward concavity of the inner surface of the blood storage chamber shell, and that is in communication with the blood outlet port and at least part of which is formed in the direction of extension of the blood outlet port.

14 Claims, 28 Drawing Sheets

U.S. PATENT DOCUMENTS

| | | |
|---|---|---|
| 4,690,762 A | 9/1987 | Katsura |
| 4,919,802 A | 4/1990 | Katsura |
| 5,458,468 A | 10/1995 | Ye et al. |
| 2007/0100273 A1 | 5/2007 | Kawarabata et al. |

FOREIGN PATENT DOCUMENTS

| | | |
|---|---|---|
| JP | 52-120593 | 10/1977 |
| JP | 64-29267 | 1/1989 |
| JP | 64-8562 | 2/1989 |
| JP | 3-62111 | 9/1991 |
| JP | 6-102088 | 12/1994 |
| JP | 3-504152 | 9/1997 |
| JP | 10-43293 | 2/1998 |
| JP | 2000-299 | 1/2000 |
| JP | 2000-84072 | 3/2000 |
| WO | 2005/056082 | 6/2005 |

CLOSED-TYPE BLOOD RESERVOIR AND EXTRACORPOREAL BLOOD CIRCULATION APPARATUS USING THE SAME

TECHNICAL FIELD

The present invention relates to closed-type blood reservoirs, and extracorporeal blood circulation apparatuses using the same, that are used for temporarily storing blood during vascular surgery that involves extracorporeal blood circulation.

BACKGROUND ART

In general, a blood reservoir for temporarily storing blood from a body is used in an extracorporeal blood circulation circuit during cardiovascular surgery that involves extracorporeal blood circulation, in order to obtain a good operative field and allow surgical operations to be performed with ease. Minimally invasive surgery has garnered increased recognition in recent years, creating a need for an extracorporeal blood circulation system that is low-invasive with regard to the individual's body and blood.

Blood reservoirs in general can be divided broadly into open-type blood reservoirs, which have hard outer casings, and closed-type blood reservoirs, in which part of the outer casing surrounding the blood storage chamber is made from a flexible material. Open-type blood reservoirs are characterized by an excellent ability to remove air bubbles that are mixed in with the blood, and they allow the volume of the stored blood to be precisely ascertained. However, open-type blood reservoirs expose blood to the outside air and thus there is the risk of adverse effects on the blood, such as blood coagulation. On the other hand, closed-type blood reservoirs in principle do not expose blood to the outside air, and thus there are fewer untoward effects on the blood. However, some drawbacks to closed-type blood reservoirs include difficulty in gauging the volume of stored blood, and less ability to remove air bubbles than open-type blood reservoirs.

An example of a closed-type blood reservoir that has means for compensating for these deficiencies is disclosed in Patent Document 1. As shown in FIG. 23, the closed-type blood reservoir discussed in Patent Document 1 has a rotated oval space, for example, formed within a housing 111. A septum 103 made from a flexible material is disposed within the housing 111, and the septum 103 partitions the space into a blood storage chamber 101 and a volume adjustment chamber 102. The part of the housing 111 that covers the blood storage chamber 101 is provided with a blood inlet port 104 for introducing blood into the blood storage chamber 101 and a blood outlet port 105 for discharging the blood that has been introduced into the blood storage chamber 101 to outside the blood storage chamber 101. The part of the housing 111 that covers the volume adjustment chamber 102 is provided with a volume adjustment liquid port 108 for injecting and discharging a volume adjustment liquid.

The volume adjustment liquid is injected into and ejected from the volume adjustment chamber 102 by a pump or a pressure difference due to difference in height for example (not shown), through the volume adjustment liquid port 108. By driving a pump to change the amount of volume adjustment liquid that is stored by the volume adjustment chamber 102 and thereby move the septum 103, the volume of the volume adjustment chamber 102 and the volume of the blood storage chamber 101 can be changed. The volume of the volume adjustment chamber 102 can be ascertained by measuring the amount of volume adjustment liquid that is moved.

Patent Document 1: JP 2000-299 A

DISCLOSURE OF INVENTION

Problem to be Solved by the Invention

The septum 103 is flexible and thus if fluid continues to flow into the blood storage chamber 101 and the volume adjustment chamber 102, it is pushed by this flow and deforms freely. At this time, negative pressure may cause the outlet port 105 to be closed off by the septum 103, as illustrated in FIG. 24.

It is an object of the invention to provide a closed-type blood reservoir, and an extracorporeal blood circulation apparatus using the same, that has a structure that inhibits blockage of the blood flow route by the septum.

Means for Solving Problem

A first closed-type blood reservoir of the invention is characterized in that it is provided with an outer shell in which a blood storage chamber shell and a volume adjustment chamber shell, each having a curved shape that is outwardly convex, are joined together and form a space therewithin, a flexible septum that is interposed between the blood storage chamber shell and the volume adjustment chamber shell and that divides the space into a blood storage chamber for storing blood and a volume adjustment chamber for storing volume adjustment liquid, a blood inlet port, a blood outlet port, and a blood storage chamber air discharge port, that are provided in the blood storage chamber shell such that they are in communication with the blood storage chamber, and a volume adjustment liquid port provided in the volume adjustment chamber shell such that it is in communication with the volume adjustment chamber, for injecting and ejecting the volume adjustment liquid to and from the volume adjustment chamber, wherein the blood inlet port and the blood outlet port each are provided tangentially to the inner surface of the blood storage chamber shell such that blood that flows into the blood storage chamber from the blood inlet port can swirl along the inner surface of the blood storage chamber shell, and wherein the closed-type blood reservoir has a first blood flow route, provided in the blood storage chamber, that is formed by an outward concavity of the inner surface of the blood storage chamber shell, and that is in communication with the blood outlet port and at least part of which is formed in the direction of extension of the blood outlet port.

A first extracorporeal blood circulation apparatus of the invention is furnished with the above closed-type blood reservoir of the invention, an adjustment liquid reservoir for storing the volume adjustment liquid that is injected into and ejected from the volume adjustment chamber, a conduit member that is connected to the volume adjustment liquid port and the volume adjustment liquid reservoir and that allows the flow rate to be adjusted, and a blood pump that is connected to the blood outlet port.

A second closed-type blood reservoir of the invention is characterized in that it is furnished with an outer shell in which a blood storage chamber shell and a volume adjustment chamber shell, each having a curved shape that is outwardly convex, are joined together and form a space therewithin, a flexible septum that is interposed between the blood storage chamber shell and the volume adjustment chamber shell, and that divides the space into a blood storage chamber for storing blood and a volume adjustment chamber for storing volume adjustment liquid, a blood inlet port, a blood outlet port, and a blood storage chamber air discharge port that are provided in the blood storage chamber shell, and a volume adjustment liquid port for injecting and ejecting the volume adjustment liquid and a volume adjustment chamber air discharge port that are provided in the volume adjustment chamber shell, wherein part of the inner circumferential portion region of the septum along the outer circumferential edge of the blood storage chamber shell forms a flat portion that is substantially flat, and the inner region of the flat portion is molded such that it can project as a curved surface toward the blood storage chamber shell or the volume adjustment chamber shell.

A second extracorporeal blood circulation apparatus of the invention is furnished with the above closed-type blood reservoir of the invention, an adjustment liquid reservoir for storing the volume adjustment liquid that is injected into and ejected from the volume adjustment chamber, a conduit member that is connected to the volume adjustment liquid port and the volume adjustment liquid reservoir and that allows the flow rate to be adjusted, and a blood pump that is connected to the blood outlet port.

A third closed-type blood reservoir of the invention is characterized in that it is furnished with an outer shell in which a blood storage chamber shell and a volume adjustment chamber shell, each having a curved shape that is outwardly convex, are joined together and form a space therewithin, a flexible septum that is interposed between the blood storage chamber shell and the volume adjustment chamber shell, and that divides the space into a blood storage chamber for storing blood and a volume adjustment chamber for storing volume adjustment liquid, a blood inlet port, a blood outlet port, and a blood storage chamber air discharge port that are provided in the blood storage chamber shell, and a volume adjustment liquid port for injecting and ejecting the volume adjustment liquid and a volume adjustment chamber air discharge port that are provided in the volume adjustment chamber shell, wherein the inner surface of the blood storage chamber shell has the shape of a rotated circular arc surface, and wherein the septum is a molded portion that is molded such that at least its central region can project as a curved surface toward the blood storage chamber shell or the volume adjustment chamber shell, and the curvature of the molded shape of the molded portion is smaller than the curvature of the blood storage chamber shell inner surface.

A third extracorporeal blood circulation apparatus of the invention is furnished with the above closed-type blood reservoir of the invention, an adjustment liquid reservoir for storing the volume adjustment liquid that is injected into and ejected from the volume adjustment chamber, a conduit member that is connected to the volume adjustment liquid port and the volume adjustment liquid reservoir and that allows the flow rate to be adjusted, and a blood pump that is connected to the blood outlet port.

BEST MODE FOR CARRYING OUT THE INVENTION

Figure 1:
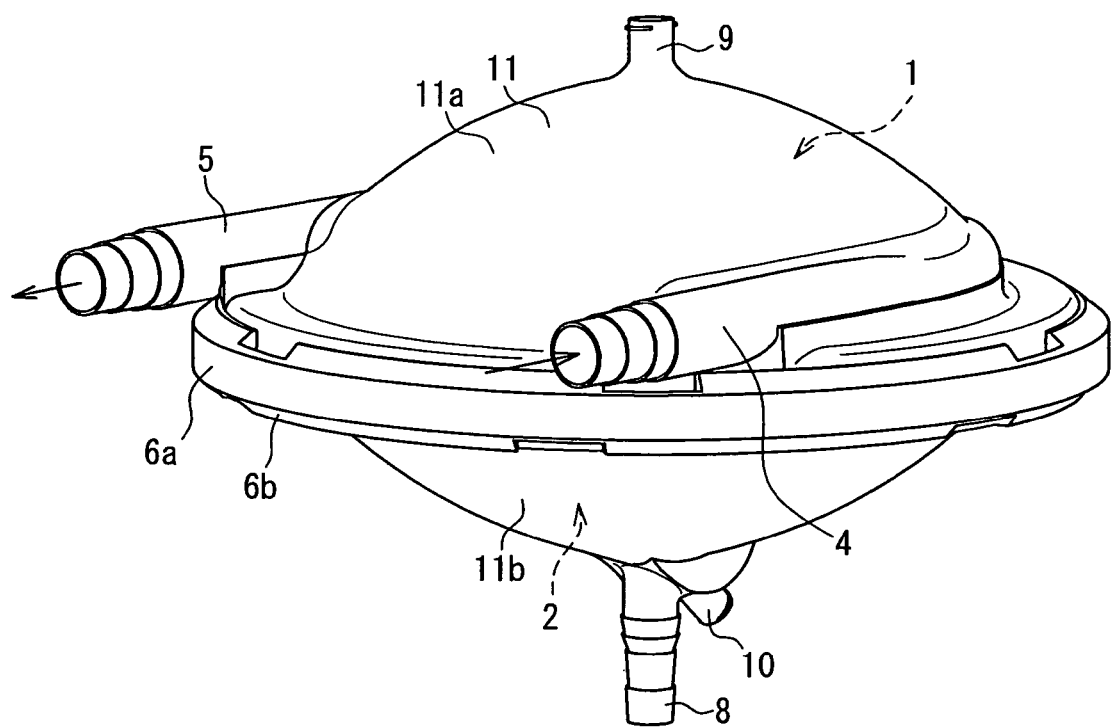
FIG. 1 is a perspective view showing an example of the closed-type blood reservoir of Embodiment 1.

With the first closed-type blood reservoir of the invention, for example, even if negative pressure causes the septum to be sucked toward the blood outlet port, due to the presence of the first blood flow route that is formed by an outward concavity of the inner surface of the housing facing the blood storage chamber, and that is in communication with the blood outlet port and at least part of which is formed in the direction of extension of the blood outlet port, the blood outlet port is prevented from being blocked off by the septum. The invention therefore can provide a closed-type blood reservoir, and an extracorporeal blood circulation apparatus using the same, in which blockage of the blood flow route is inhibited.

In a favorable example of the first closed-type blood reservoir of the invention, the closed-type blood reservoir has a second blood flow route, provided in the blood storage chamber, that is formed by an outward concavity of the inner surface of the blood storage chamber shell, and that is in communication with the blood inlet port and at least part of which is formed in the direction of extension of the blood inlet port.

It is also possible that the first blood flow route and the second blood flow route are connected to one another, and form a single continuous blood flow route.

In a favorable example of the first closed-type blood reservoir of the invention, the blood inlet port and the blood outlet port open in the same direction and are provided in the blood storage chamber shell such that their center axes are parallel.

In a favorable example of the first closed-type blood reservoir of the invention, a portion of the inner surface of the blood storage chamber shell that is located between the first blood flow route and the second blood flow route in the circumferential direction forms part of a continuous curved surface from the circumferential edge portion of the inner surface toward its center portion.

It is also possible to provide an extracorporeal blood circulation apparatus using an example of the first closed-type blood reservoir of the invention. Because this extracorporeal blood circulation apparatus uses an example of the first closed blood reservoir of the invention, blockage of the blood flow route is inhibited.

With the second closed-type blood reservoir of the invention, the circumferential portion of the septum forms a flat portion, thereby securing a gap of a predetermined size between the blood storage chamber shell inner surface and the septum at the circumferential portion of the blood storage chamber shell, and thus the blood outlet port is prevented from being blocked off by the septum. Consequently, when loading priming liquid in preparation for use, bubbles that remain at the circumferential portion of the blood storage chamber can be removed with ease.

With the third closed-type blood reservoir of the invention, it is possible to obtain a dimensional relationship in which the spacing between the blood storage chamber shell and the septum is a maximum at the center portion and decreases toward the circumferential portion. Thus, a gap of a predetermined size can be secured between the blood storage chamber shell inner surface and the septum and prevents the blood outlet port from being closed off by the septum. Further, when the septum moves in conjunction with a change in stored blood volume, the blood storage chamber shell and the septum draw increasingly close to one another starting from the circumferential portion toward the center portion. Thus, the removal of bubbles that remain at the circumferential portion of the blood storage chamber can be carried out with ease. In a preferable example of this closed-type blood reservoir, part of the region of the circumferential portion of the septum along the inner side of the outer circumferential edge of the blood storage chamber shell forms a flat portion that is substantially flat.

A fourth closed-type blood reservoir of the invention is characterized in that it is furnished with an outer shell in which a blood storage chamber shell and a volume adjustment chamber shell that are outwardly convex are joined together and form a space therewithin, a flexible septum that is interposed between the blood storage chamber shell and the volume adjustment chamber shell, and that divides the space into a blood storage chamber for storing blood and a volume adjustment chamber for storing volume adjustment liquid, a blood inlet port, a blood outlet port, and a blood storage chamber air discharge port that are provided in the blood storage chamber shell, and a volume adjustment liquid port for injecting and ejecting the volume adjustment liquid and a volume adjustment chamber air discharge port that are provided in the volume adjustment chamber shell, wherein the volume adjustment chamber shell has a shape in which its center portion is an apex, and wherein the volume adjustment liquid port is provided in the center portion of the volume adjustment chamber shell and the volume adjustment chamber air discharge port is provided adjacent to the volume adjustment liquid port.

With the fourth closed-type blood reservoir of the invention, the volume adjustment chamber air discharge port is provided adjacent to the volume adjustment liquid port in the center portion, which is an apex, of the volume adjustment chamber shell, and thus during priming its orientation can be adjusted easily to keep the volume adjustment chamber air discharge port at the highest point of the volume adjustment chamber. By doing this, the air that remains within the volume adjustment chamber during priming collects near the volume adjustment chamber air discharge port and is discharged rapidly, allowing priming to be carried out efficiently.

In a favorable example of the fourth closed-type blood reservoir of the invention, an air discharge port opening that is formed in the volume adjustment chamber shell by providing the volume adjustment chamber air discharge port is disposed within a concavity that is provided from the inner wall surface of the volume adjustment chamber shell toward the outside.

It is also possible to provide an extracorporeal blood circulation apparatus using the preferable example of the fourth closed-type blood reservoir of the invention. This extracorporeal blood circulation apparatus is furnished with an example of the fourth closed-type blood reservoir of the invention, an adjustment liquid reservoir for storing the volume adjustment liquid that is injected into and ejected from the volume adjustment chamber, a conduit member that is connected to the volume adjustment liquid port and the volume adjustment liquid reservoir and that allows the flow rate to be adjusted, and a blood pump that is connected to the blood outlet port.

Embodiment 1

Figure 2:
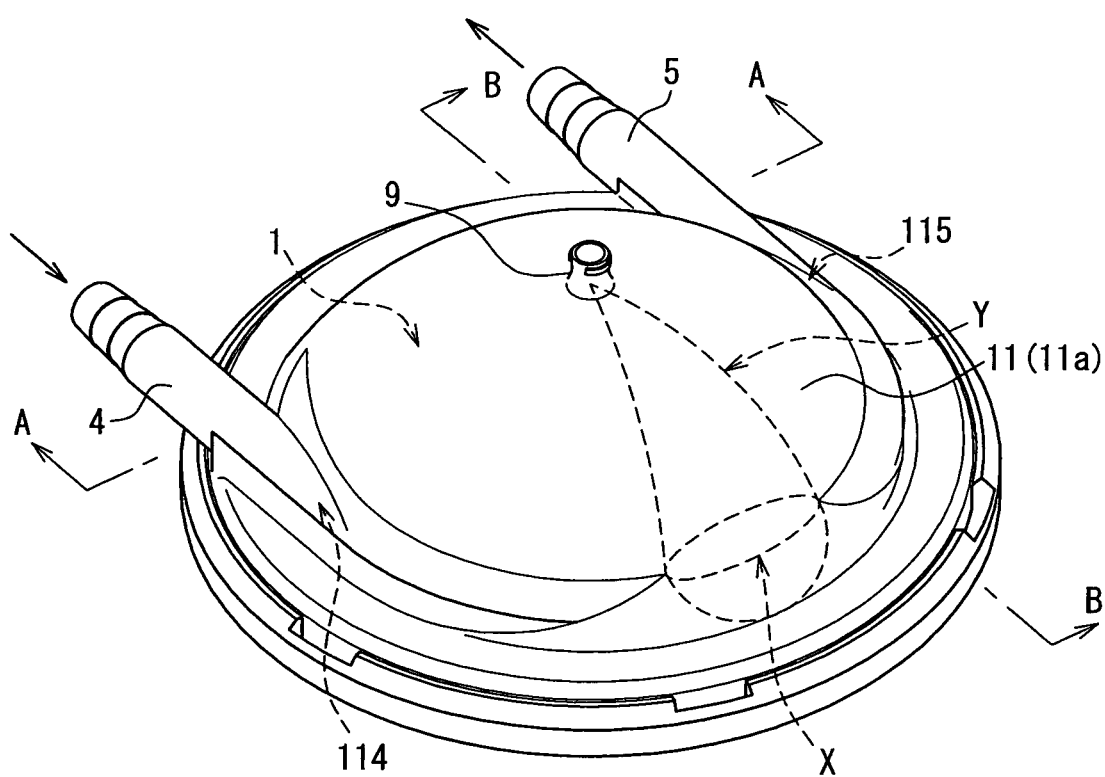
FIG. 2 is another perspective view of the closed-type blood reservoir shown in FIG. 1.

In Embodiment 1, an example of a first closed-type blood reservoir (hereinafter, also referred to simply as "blood reservoir") of the invention is described in reference to the drawings. FIG. 1 and FIG. 2 are perspective views that show examples of the closed-type blood reservoir of this embodiment.

As shown in FIG. 1 and FIG. 2, the closed-type blood reservoir of this embodiment is provided with an outer shell 11 that is formed by the joining of a first joining portion 6a of a blood storage chamber shell 11a, which has a curved shape that is outwardly convex, and a second joining portion 6b of a volume adjustment chamber shell 11b, which also has a curved shape that is outwardly convex. The outer shell 11 contains within it a space of substantially rotated oval-shape. The blood storage chamber shell 11a is provided with a blood inlet port 4 for introducing blood, a blood outlet port 5 for discharging blood, and a blood storage chamber air discharge port 9. These are in communication with a blood storage chamber 1, which is discussed later. The volume adjustment chamber shell 11b is provided with a volume adjustment liquid port 8 for introducing and discharging a volume adjustment liquid, and a volume adjustment chamber air discharge port 10. These are in communication with a volume adjustment chamber 2, which is described later.

Figure 3A:
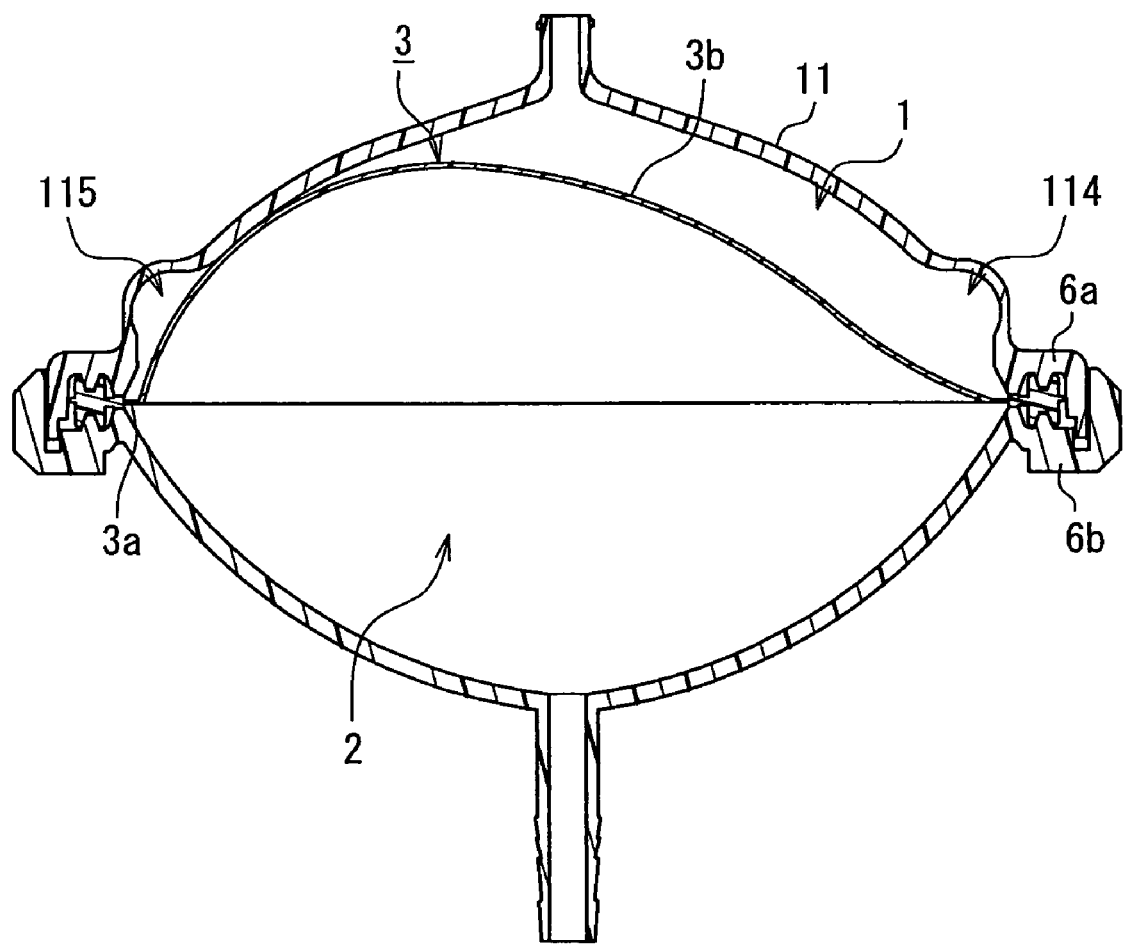
FIG. 3A is a cross-sectional view taken along the line A-A in FIG. 2.

FIG. 3A is a cross-sectional view taken along the line A-A in FIG. 2. As shown in FIG. 3A, a flexible septum 3 that is made from a flexible material is provided in the space within the outer shell 11, and divides the inside of the outer housing 11 into the blood storage chamber 1 and the volume adjustment chamber 2. The blood storage chamber 1 is used for temporarily storing blood, and the volume adjustment chamber 2 is used for storing liquid for volume adjustment. The blood storage chamber 1 and the volume adjustment chamber 2 are separated by the septum 3 and are not in contact with one another.

As shown in FIG. 1 and FIG. 2, the outer shell 11 has a substantially circular shape when the closed-type blood reservoir is viewed straight on from the blood storage chamber side. The blood inlet port 4 and the blood outlet port 5 both are provided in the circumferential portion, for example, of the curved, outwardly convex portion of the blood storage chamber shell 11a, tangentially to the inner surface of the housing 11 facing the blood storage chamber 1 (inner surface of the blood storage chamber shell 11a). Thus, blood that flows into the blood storage chamber 1 from the blood inlet port 4 circles within the blood storage chamber 1 and is discharged from the blood outlet port 5. Air bubbles that are mixed in with the blood that flows into the blood storage chamber 1 from the blood inlet port 4 collect at the central top portion (apex) of the blood storage chamber 1 and are separated from the blood due to the sudden increase in the cross sectional area of the flow route and the action of the centripetal force from the rotational flow. The collected air bubbles can be discharged through the blood storage chamber air discharge port 9, which is provided for the purpose of discharging air bubbles. The closed-type blood reservoir thus sequesters air bubbles and ensures the safety of extracorporeal blood circulation. Further, when priming, air bubbles within the blood storage chamber 1 are removed efficiently, and thus the time required to prepare for extracorporeal blood circulation is shortened.

As shown in FIG. 1 and FIG. 2, the blood inlet port 4 and the blood outlet port 5 open in the same direction, and preferably they are provided in the blood storage chamber shell 11a such that their center axes are parallel. This is because a relatively long blood swirling distance can be secured and it is easy to connect tubes, for example, to the blood inlet port 4 and the blood outlet port 5. This also improves handling of the blood reservoir when tubes or the like are connected, and the blood reservoir can be produced with ease.

Here, the "swirling distance" is the distance from the opening on the blood storage chamber 1 side of the blood inlet port 4 to the opening on the blood storage chamber 1 side of the blood outlet port 5, and is the distance along the inner surface of the outer shell 11 facing the blood storage chamber 1 (the inner surface of the blood storage chamber shell 11a).

Figure 3B:
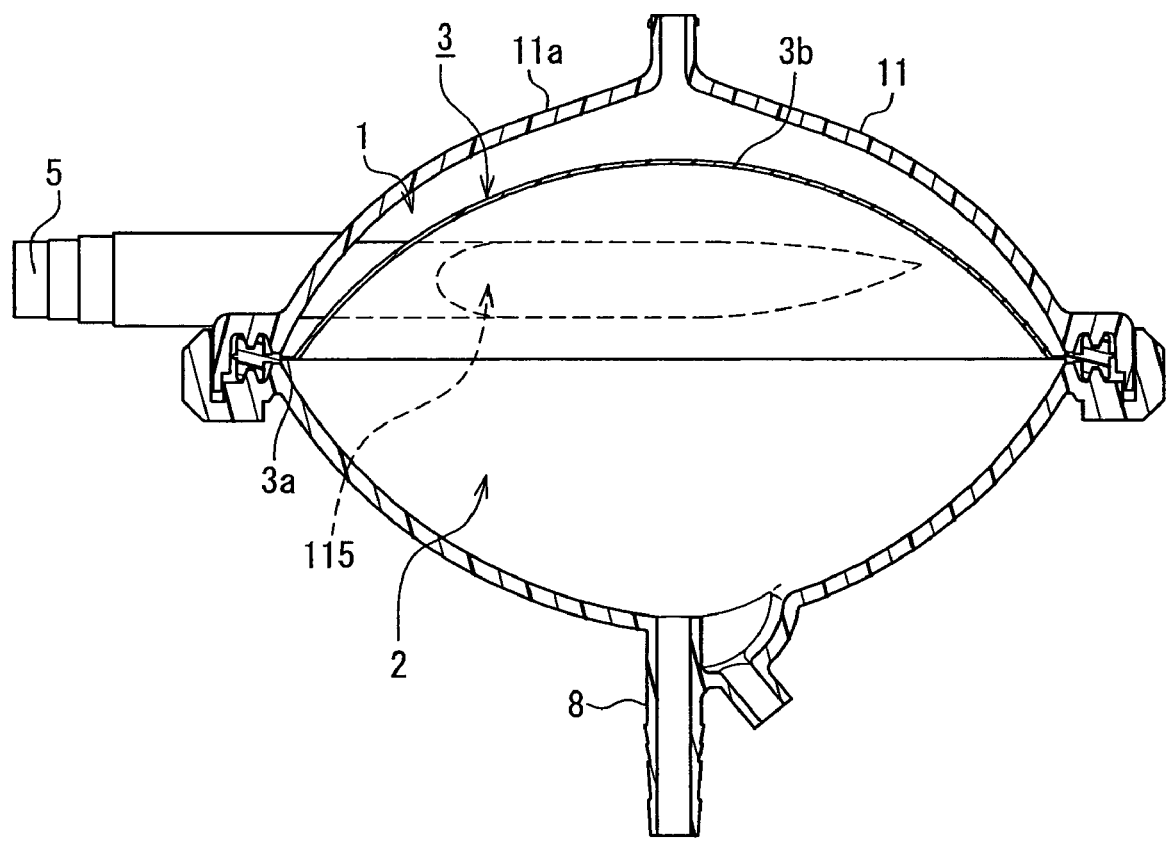
FIG. 3B is a cross-sectional view taken along the line B-B in FIG. 2.

FIG. 3B is a cross-sectional view taken along the line B-B in FIG. 2. As shown in FIG. 2 and FIG. 3B, the closed-type blood reservoir is provided with a first blood flow route 115 within the blood storage chamber 1 by forming an outward concavity in the inner surface of the blood storage chamber shell 11a. The first blood flow route 115 is in communication with the blood outlet port 5, and part of it is present in the direction of extension of the blood outlet port 5 as well as along the inner surface of the housing 11, and thus at least part of the lengthwise direction of the first blood flow route 115 is aligned with the lengthwise direction of the blood outlet port 5. Thus, even if negative pressure causes the septum 3 to be sucked toward the blood outlet port 5, the presence of the first blood flow route 115 prevents the blood outlet port 5 from being closed off by the septum 3.

In other words, as shown in FIG. 3A, when the septum 3 is drawn toward the blood outlet port 5, the septum 3 is supported on the inner surface of the blood storage chamber shell 11a surrounding the first blood flow route 115. Thus, even if the septum 3 has drawn near the inner surface of the blood storage chamber shell 11a, the first blood flow route 115 secures the space around the blood storage chamber 1 side opening of the blood outlet port 5, and thereby secures the blood flow route. As a result, the extracorporeal blood circulation flow route is kept from being closed off.

In the example shown in FIG. 2 and FIG. 3B, the blood outlet port 5 is provided at a circumferential edge portion of the blood storage chamber shell 11a, and thus the first blood flow route 115 is present in the blood storage chamber 1 along the circumferential edge portion of the blood storage chamber shell 11a. Further, the outwardly depressed portion of the inner surface of the blood storage chamber shell 11a and the inner circumferential surface of the blood outlet port 5 are linked with substantially no difference in level.

As shown in FIGS. 1 through 3A, the closed-type blood reservoir of this embodiment is provided with a second blood flow route 114 within the blood storage chamber 1 that is formed by an outward concavity in the inner surface of the blood storage chamber shell 11a. The second blood flow route 114 is in communication with the blood inlet port 4, part of it is present in the direction of extension of the blood inlet port 4, and it is present along the inner surface of the blood storage chamber shell 11a, and thus at least part of the lengthwise direction of the second blood flow route 114 (the same direction as the direction in which the blood advances forward) is the same as the lengthwise direction of the blood inlet port 4.

Even if the blood storage chamber 1 is not provided with the second blood flow route 114, due to positive pressure from the blood that flows into the blood storage chamber 1 from the blood inlet port 4, blood can be introduced into the blood storage chamber 1. When the blood storage chamber 1 is furnished with the second blood flow route 114, however, the flow of blood into the blood storage chamber 1 proceeds smoothly and blood damage and pressure loss, for example, can be inhibited, and this is favorable.

As illustrated by FIG. 2, the first blood flow route 115 and the second blood flow route 114 are not connected. A portion X located between the first blood flow route 115 and the second blood flow route 114 in the circumferential direction on the inner surface of the blood storage chamber shell 11a forms a portion of a curved surface Y that is continuous from the circumferential edge portion to the center of the blood storage chamber shell 11a. In other words, the portion X is not concave outward. This shape allows the separation of blood and gas to be carried out more favorably and there is increased safety, and thus is preferable. The reason for this is discussed below.

In instances where blood is flowing into the blood storage chamber 1 relatively slowly, the air bubbles mixed in with the blood readily move to areas within the blood storage chamber 1 where the flow rate is slow, that is, the central upper portion (apex) of the blood storage chamber 1, due to their buoyancy. Similarly, air bubbles mixed in with the blood readily move to the central upper portion also when the diameter of the blood storage chamber 1 is large, the more adequately the separation of air and liquid occurs due to the buoyancy of the air bubbles, regardless of the flow rate of the blood. Thus, in this case, the danger that air bubbles will be sent out from the blood storage chamber 1 is low.

However, in instances where the blood is flowing into the blood storage chamber 1 relatively quickly, the separation of air and liquid due to the buoyancy of the air bubbles does not occur sufficiently, and there is an increased risk that air bubbles will be sent out from the blood reservoir. When air bubbles that are sent out from the blood reservoir enter into a patient's body, the patient is at increased risk for air embolus, for example, and the safety of the extracorporeal blood circulation drops. The same risk is also present when the diameter of the blood storage chamber 1 is relatively small.

However, when, like in the closed-type blood reservoir shown in FIG. 2, the first blood flow route 115 and the second blood flow route 114 are formed such that they are not connected to one another, and the part X between the first blood flow route 115 and the second blood flow route 114 forms a portion of the curved surface Y, which is continuous from the circumferential edge portion to the center portion of the inner surface of the bowl-shaped portion of the blood storage chamber shell 11a (the curved portion that is outwardly convex), the part X is linked with the center portion without a difference in level between them, and thus air bubbles easily move toward the central upper part of the blood storage chamber, in which the blood flow is relatively slow. Along with this movement of the air bubbles, the separation of air and liquid due to the buoyancy of the air bubbles can occur more easily. Since the separation of air and liquid occurs more readily, it is harder for air bubbles to flow out from the blood reservoir and the safety of the blood storage chamber increases.

There are no particular restrictions regarding the length of the first blood flow route 115 (the part of the inner surface of the housing that is concave outward), but preferably it is ⅛ to ⅓ of the swirling distance. This is because, although from the standpoint of the air/liquid separation it is preferable that the swirling distance that occupies the section of the inner surface of the blood storage chamber shell 11a that is concave outward is short, the effect of preventing flow route blockage cannot be sufficiently obtained when the length of the first blood flow route 115 is too short.

The material that forms the outer shell 11 of the blood reservoir may be hard or soft, but in terms of the ability to retain its shape and pass light, preferably it is a hard shell made from polycarbonate, polyethylene terephthalate, or acrylic resin, for example, that does not break easily.

The septum 3 is flexible and resistant to pressure and preferably has excellent processability, and preferably is PVC, polyolefin, or polytetrafluoroethylene.

Figure 4A:
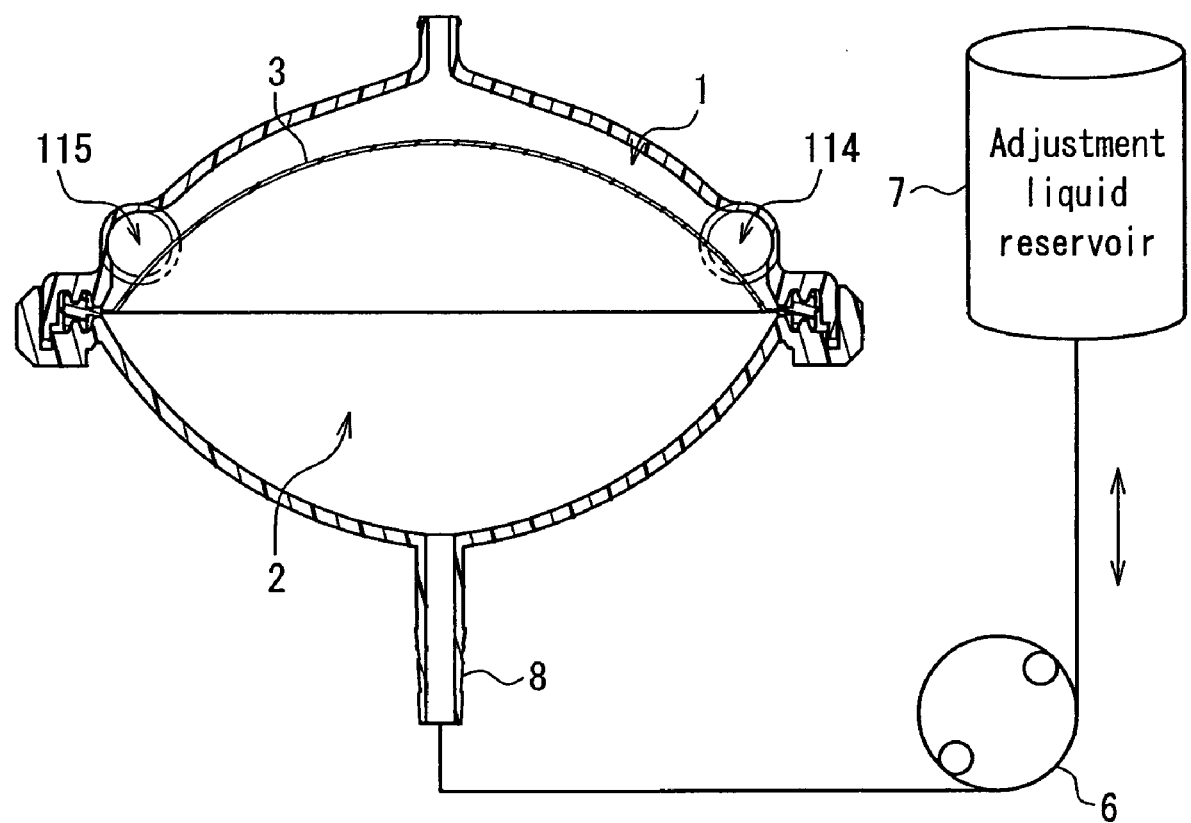
FIG. 4A is a cross-sectional view that illustrates the operation of the closed-type blood reservoir.

As shown in FIG. 4A, a volume adjustment liquid port 8 for injecting and ejecting a volume adjustment liquid is connected to an adjustment liquid reservoir 7 via a pump 6. Due to the pump 6, the volume adjustment liquid is sent back and forth between the volume adjustment chamber 2 and the adjustment liquid reservoir 7. By driving the pump 6 to change the amount of volume adjustment liquid that is stored in the volume adjustment chamber 2 and thereby move the septum 3, the volume of the volume adjustment chamber 2 can be changed and therefore the volume of the blood storage chamber 1 can be changed. As long as the volume of the volume adjustment chamber 2 prior to starting blood storage is known, then the amount of change in that volume can be understood as the amount of change in the volume of the blood storage chamber 1, and it is possible to ascertain the amount of blood that is stored outside the body. The change in the volume of the volume adjustment chamber 2 can be known by measuring the change in the amount of volume adjustment liquid that is kept in the adjustment liquid reservoir 7.

Figure 4B:
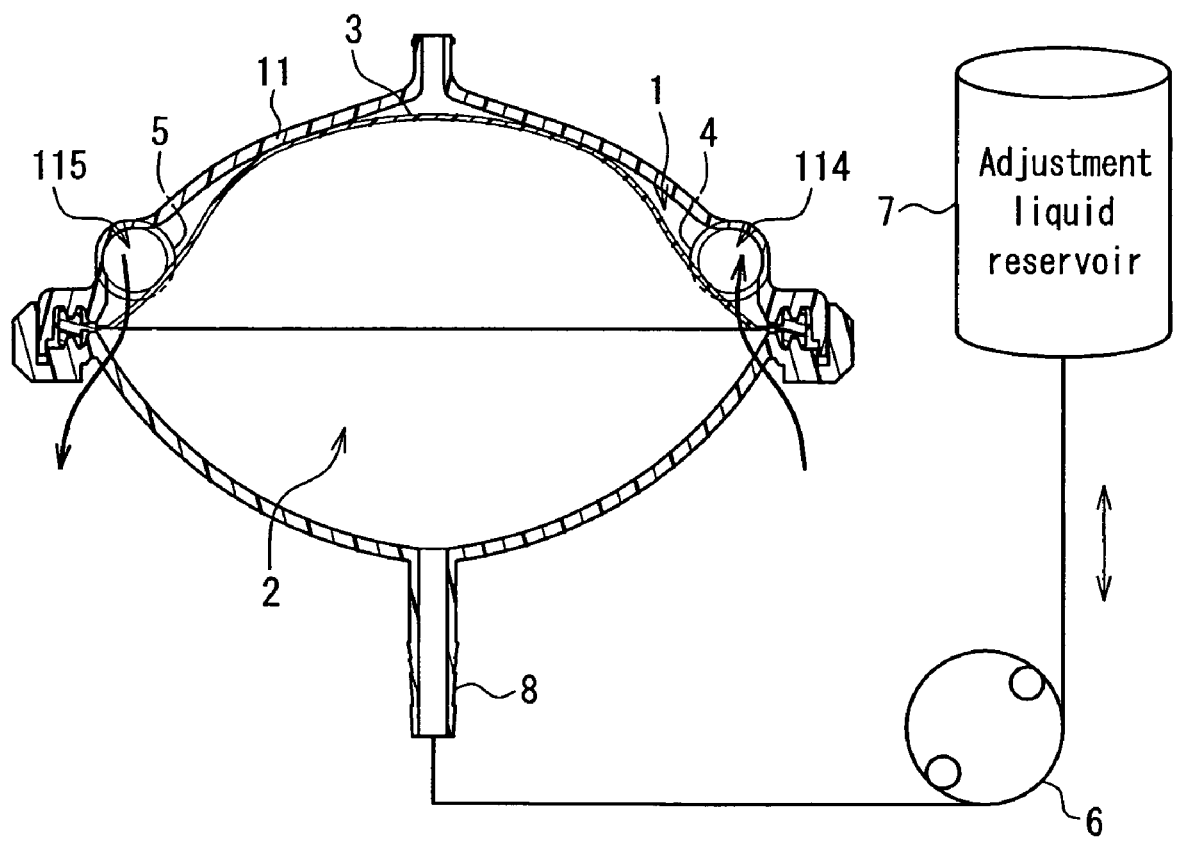
FIG. 4B is a cross-sectional view that illustrates the operation of the closed-type blood reservoir.
Figure 4C:
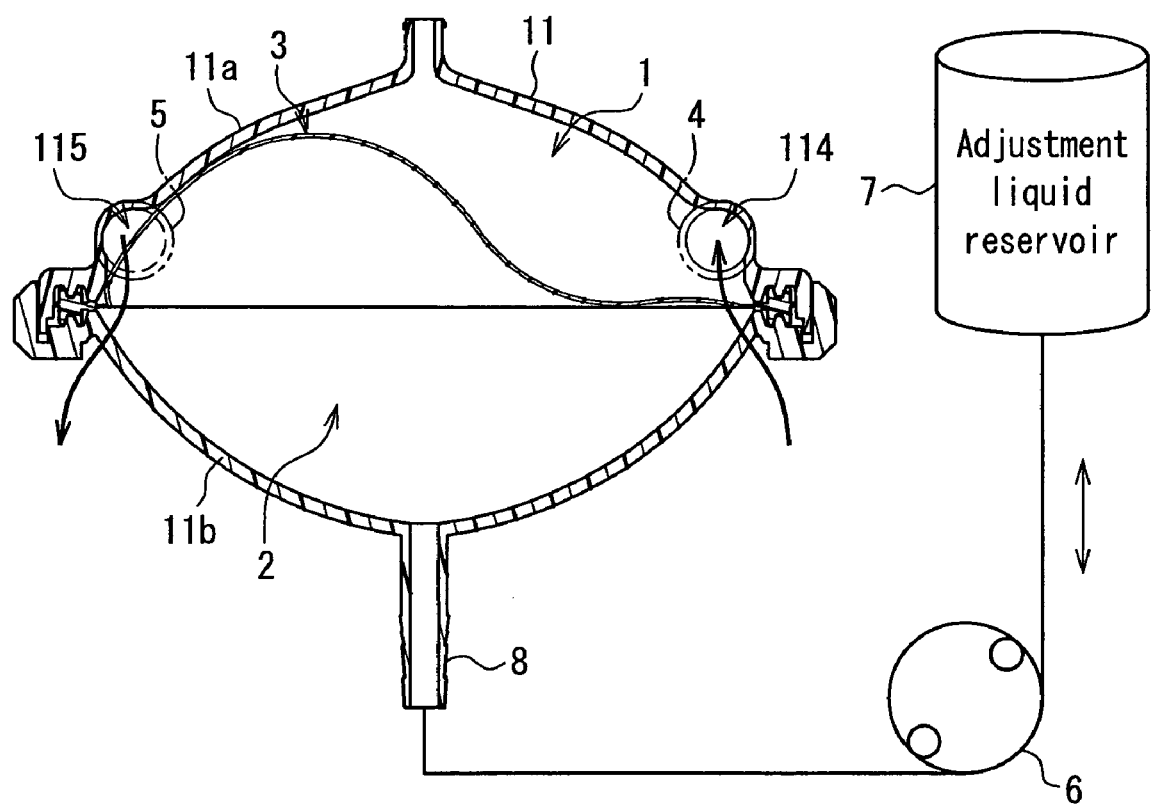
FIG. 4C is a cross-sectional view that illustrates the operation of the closed-type blood reservoir.

Next, the operation of the closed-type blood reservoir is described with reference to FIGS. 4B and 4C. It should be noted that for the sake of facilitating understanding, FIGS. 4B and 4C show a closed blood reservoir 20 in cross section. Thus, for the sake of illustration, the blood inlet port 4 and the blood outlet port 5 are depicted by imaginary lines. When using this blood reservoir, first, as shown in FIG. 4B, the pump 6, for example, is used to fill the volume adjustment chamber 2 with an adjustment liquid such as saline solution from the adjustment liquid reservoir 7. The adjustment liquid is filled until the septum 3 almost touches the inner surface of the outer shell 11 (the blood storage chamber shell) facing the blood storage chamber 1. Next, the minimum necessary amount of priming solution is filled into the extracorporeal blood circulation flow route, which includes the blood storage chamber 1.

When extracorporeal blood circulation is started, blood that has been removed from the body is introduced into the blood storage chamber 1 through the blood inlet port 4, and passes through the blood outlet port 5 and is discharged from the blood storage chamber 1. At this time, when the pump 6 causes the saline solution of the volume adjustment chamber 2 to be discharged toward the adjustment liquid reservoir 7, the septum 3 is moved toward the volume adjustment chamber 2 in accordance with the amount of saline solution that has been ejected from the volume adjustment chamber 2, and the volume of the blood storage chamber 1 increases. In other words, an amount of blood that corresponds to the amount of saline solution that has been sent to the adjustment liquid reservoir 7 by the pump 6 is stored in the blood storage chamber 1 as the amount of change. That amount can be ascertained accurately from the adjustment liquid reservoir 7.

Conversely, when saline solution is sent to the volume adjustment chamber 2 from the adjustment liquid reservoir 7 by the pump 6, the septum 3 moves toward the blood storage chamber 1 in correspondence with that amount, and the volume of the blood storage chamber 1 decreases. As a result, the blood that is stored in the blood storage chamber 1 is discharged from the blood storage chamber 1 and ultimately returns to the body. That amount can be ascertained accurately from the adjustment liquid reservoir 7.

As described above, the volume of the blood storage chamber 1 can be changed easily, and, moreover, the change in volume of the blood storage chamber 1, that is, the volume of stored blood, can be ascertained readily. Consequently, for extracorporeal blood circulation it is not necessary to select a blood reservoir with an appropriate volume each time depending on the patient conditions, and by readying a blood reservoir with a certain degree of volume it is possible to handle small to large volumes. Furthermore, it is possible to instantaneously increase or decrease the amount of stored blood depending on the state of extracorporeal blood circulation, and it is possible to select the minimum necessary volume for the conditions, and thus the amount of patient blood that is subjected to extracorporeal blood circulation can be reduced.

On the other hand, because the septum 3 is flexible when the flow of fluid to the blood storage chamber 1 and the volume adjustment chamber 2 is continued the septum 3 is pressed by this flow and deforms freely, and particularly in instances where there is little blood stored in the blood storage chamber 1, the septum 3 is drawn toward the blood outlet port 5, as shown by FIG. 4C. With the configuration of this embodiment, however, even if the septum 3 is drawn to the blood outlet port 5 by negative pressure, the presence of the first blood flow route 115 formed by the outward concavity of the inner surface of the blood storage chamber shell 11a, which is in communication with the blood outlet port 5 and at least part of which is formed in the direction of extension of the blood outlet port 5, keeps the blood outlet port 5 from being closed off by the septum 3, and this secures the flow route for the blood.

The shape of the first blood flow route 115 is not limited to the shape shown in the drawings, and can be set appropriately depending on the shape and dimensions of the blood storage chamber shell 11a, and the material and placement of the septum 3. That is to say, it is only necessary that the first blood flow route 115 communicate with the blood outlet port 5 as an outwardly concave space, and that at least part of it lays in the direction of extension of the blood outlet port 5. Additionally, in order to keep the blood outlet port 5 and the first blood flow route 115 from being closed off within the range of driving conditions of the pump 6, for example, it is sufficient for the septum 3 to be supported by the inner surface of the blood storage chamber shell 11a around the first blood flow route 115, which is formed as a groove, for example.

Figure 5:
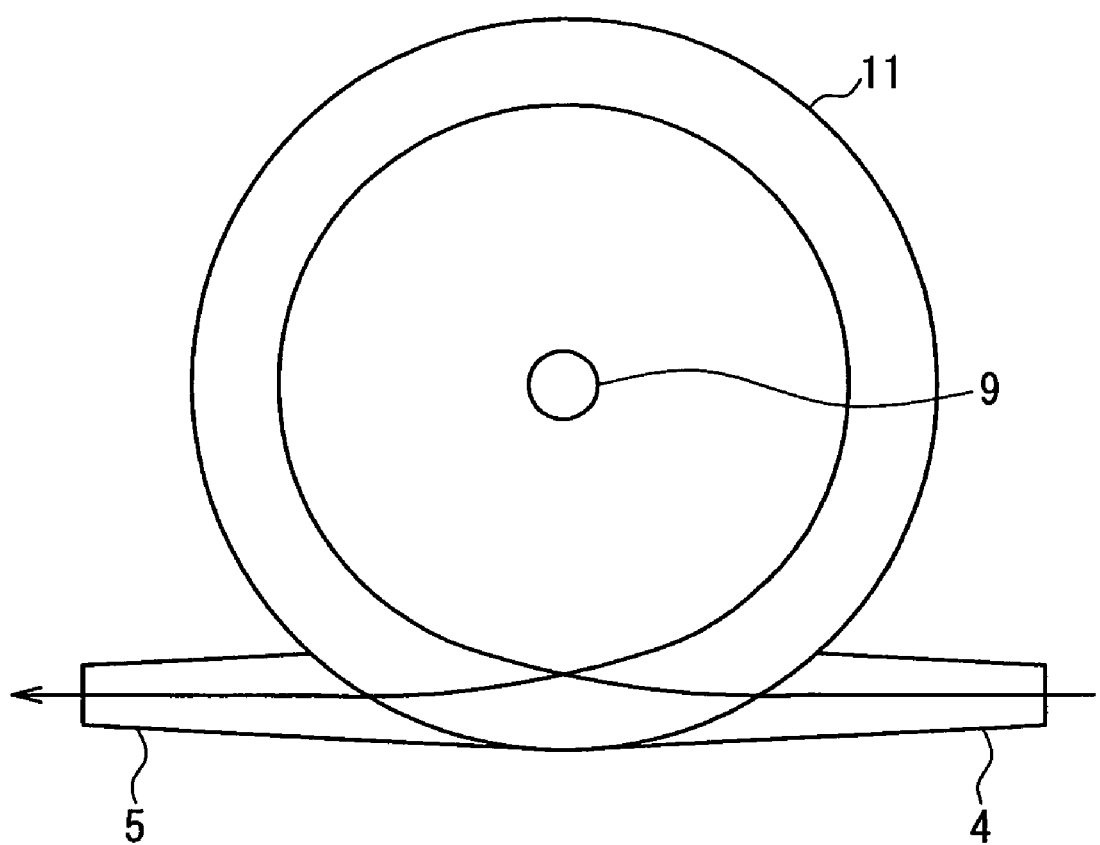
FIG. 5 is an overview showing another example of the closed-type blood reservoir of Embodiment 1.

As long as the blood that flows into the blood storage chamber 1 from the blood inlet port 4 can swirl within the blood storage chamber 1, then, as shown in FIG. 5, it is also possible for the blood inlet port 4 and the blood outlet port 5 to be provided in such a manner that that the center axis of the blood inlet port 4 and the center axis of the blood outlet port 5 are coaxial.

In the example described that was using FIGS. 1 through 5, a space of substantially rotated oval-shape exists within the outer shell, but it is also possible for this space to be substantially spherical in shape. Further, in the example that was described using FIGS. 1 through 5, part of both the first blood flow route 115 and the second blood flow route 114 lay in the direction of extension of the blood outlet port 5 and the blood inlet port 4, and the first blood flow route 115 and the second blood flow route 114 are along the inner surface of the blood storage chamber shell 11a, but the closed-type blood reservoir of this embodiment is not limited to this implementation. It is also possible for the entire length of at least one of the first blood flow route 115 and the second blood flow route 114 to be formed in the direction of extension of the blood outlet port 5 and the blood inlet port 4. In other words, it is also possible for both the first blood flow route 115 and the second blood flow route 114 to be shorter in their lengthwise direction than in the example that was described using FIGS. 1 through 5.

Embodiment 2

Figure 6:
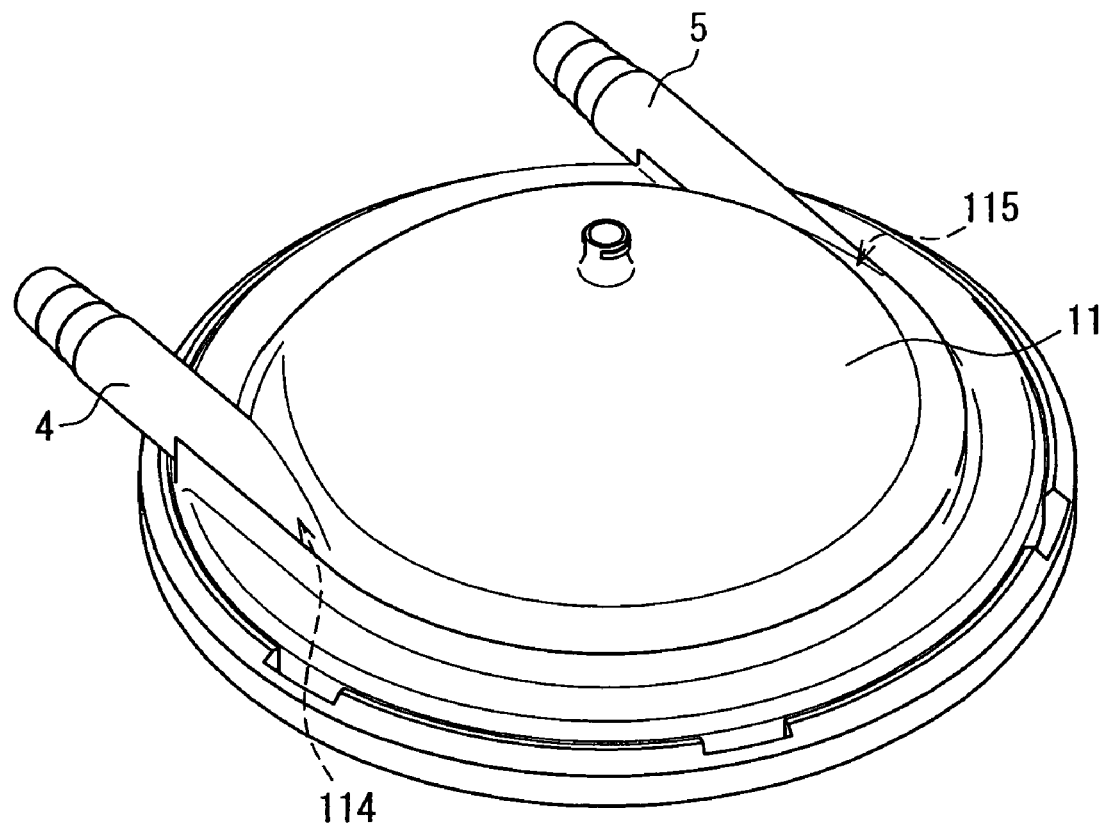
FIG. 6 is a perspective view showing an example of the closed-type blood reservoir of Embodiment 2.

In Embodiment 2, another example of the first closed-type blood reservoir of the invention is described with reference to the drawings. FIG. 6 is a perspective view showing the closed-type blood reservoir of this embodiment.

With the closed-type blood reservoir of this embodiment, the first blood flow route 115 and the second blood flow route 114 are linked to one another and form a single continuous blood flow route. Other than this, the closed-type blood reservoir of this embodiment is the same as that of Embodiment 1, and the closed-type blood reservoir of this embodiment achieves the same effects as the closed-type blood reservoir of Embodiment 1 due to their similar configurations.

If the rate at which blood flows into the blood storage chamber 1 is made relatively slow, then, even when the closed-type blood reservoir of this embodiment is used, extracorporeal blood circulation can be performed safely without air bubbles being sent out from the blood reservoir. Similarly, extracorporeal blood circulation can be performed safely even in a case where the blood storage chamber is set to a large diameter so as to more adequately separate air from liquid due to the buoyancy of the air bubbles, regardless of the flow rate of the blood.

Embodiment 3

Figure 7:
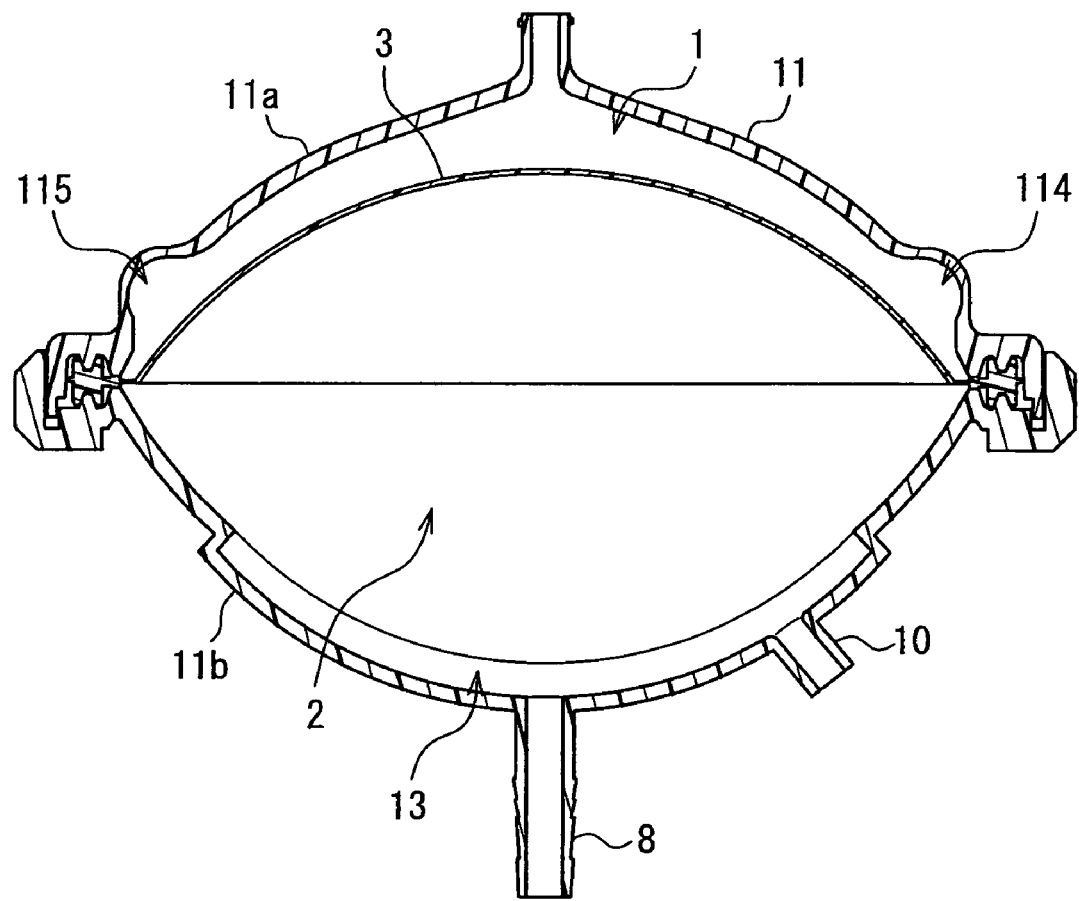
FIG. 7 is a cross-sectional view showing an example of the closed-type blood reservoir of Embodiment 3.

In Embodiment 3, a yet further example of the first closed-type blood reservoir of the invention is described with reference to the drawings. FIG. 7 is a cross-sectional view showing the closed-type blood reservoir of this embodiment.

As shown in FIG. 7, the closed-type blood reservoir of this embodiment has a blockage prevention flow route 13, provided in the volume adjustment chamber 2, that is formed by an outward concavity in the inner surface of the volume adjustment chamber shell 11b facing the volume adjustment chamber 2, and the volume adjustment liquid port 8 and the volume adjustment chamber air discharge port 10 are provided in the housing 11 in such a manner that they communicate with the blockage prevention flow route 13. The blockage prevention flow route 13 for example has a linear shape with a constant width. Other than this, the closed-type blood reservoir of this embodiment is the same as that of Embodiment 1, and the closed-type blood reservoir of this embodiment achieves the same effects as the closed-type blood reservoir of Embodiment 1 due to their similar configurations.

Since the closed-type blood reservoir of this embodiment is provided with the blockage prevention flow route 13 within the volume adjustment chamber 2, there is reduced risk that the volume adjustment liquid port 8 will be closed-type off by the septum 3 even if the septum 3 abuts against a portion of the housing inner surface forming the volume adjustment chamber 2. The abutting septum 3 is supported by the inner surface of the volume adjustment chamber shell 11b surrounding the blockage prevention flow route 13, and thus the presence of the blockage prevention flow route 13 secures the space around the volume adjustment chamber 2 side opening of the volume adjustment liquid port 8, and this secures a flow route for the adjustment liquid.

Embodiment 4

Embodiment 4 describes an example of a first extracorporeal blood circulation apparatus of the invention that is formed using a closed-type blood reservoir that is described in Embodiments 1 to 3.

Figure 8:
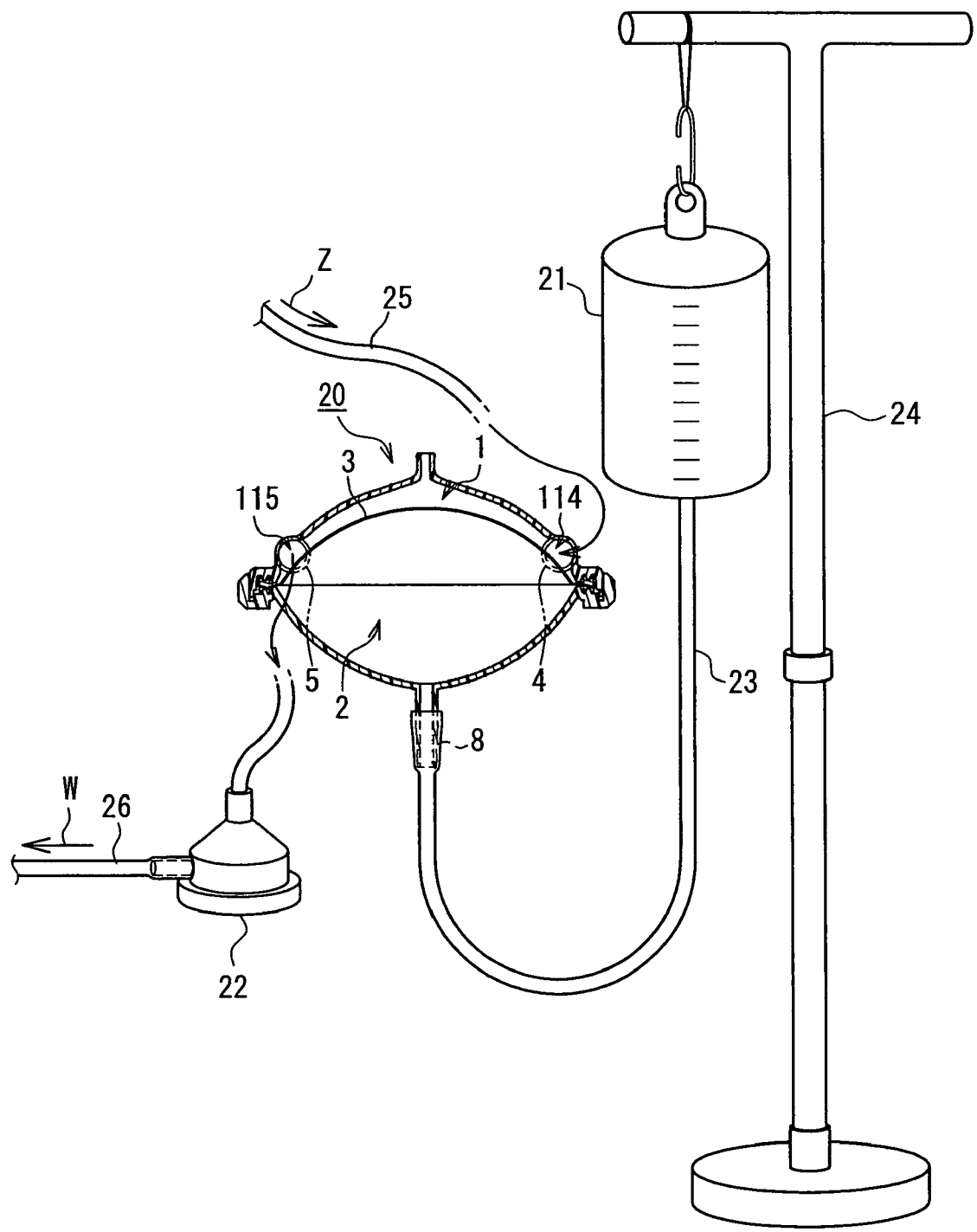
FIG. 8 is a schematic view showing an example of the extracorporeal blood circulation apparatus of Embodiment 4.

FIG. 8 shows an example of the extracorporeal blood circulation apparatus of this embodiment. It should be noted that for the sake of facilitating understanding, in FIG. 8, a closed-type blood reservoir 20 is shown in cross section. Thus, for the sake of simplifying the drawing, the blood inlet port 4 and the blood outlet port 5 are drawn with imaginary lines.

As shown in FIG. 8, this example of the extracorporeal blood circulation apparatus of the embodiment is provided with the closed-type blood reservoir 20 of the invention, an adjustment liquid reservoir 21, and a blood pump 22 such as a centrifugal pump. The adjustment liquid reservoir 21 is connected to the volume adjustment liquid port 8 of the closed-type blood reservoir 20 through a flexible adjustment liquid route tube 23, which is a conduit member. The inlet opening of the blood pump 22 is connected to the blood outlet port 5 of the closed-type blood reservoir 20. The adjustment liquid reservoir 21 is supported by a support fitting 24 that allows its height relative to the closed-type blood reservoir 20 to be adjusted. A flexible blood-removal side tube 25 that is connected to the site where blood is withdrawn from the body is connected to the blood inlet port 4 of the closed-type blood reservoir 20, and blood flows in as shown by the arrow Z. A flexible blood-return side tube 26 that is connected to the site where blood is returned is connected to the ejection opening of the blood pump 22, and blood flows out as shown by the arrow W.

The adjustment liquid reservoir 21 has the function of storing the volume adjustment liquid that is injected to and ejected from the volume adjustment chamber 2 of the closed-type blood reservoir 20. The adjustment liquid route tube 23 is designed such that the cross-sectional area of its flow route can be varied. For example, if the adjustment liquid route tube 23 is constituted by a tube that is flexible, then the tube can be clamped with forceps to block, open, or partially block, the flow route, allowing the cross-sectional area of the flow route to be altered. It is also possible to adopt a structure in which the adjustment liquid route tube 23 is provided with a flow route adjustment member for changing the flow route cross-sectional area, such as a cock, within its flow route, and its flow route cross-sectional area is changed with this flow route adjustment member.

The adjustment liquid reservoir 21 has a measurement portion, such as a scale, for measuring the amount of volume adjustment liquid that is being stored.

By changing the position where the adjustment liquid reservoir 21 is supported by the support fitting 24 in order to adjust the height of the adjustment liquid reservoir 21 with respect to the site where blood is withdrawn from the body, that is, to adjust the height difference of the volume adjustment liquid, it is possible to increase or decrease the amount of volume adjustment liquid that is stored in the volume adjustment chamber 2. Thus, the volume of the blood storage chamber 1 is adjusted by moving the septum 3. As long as the volume of the volume adjustment chamber 2 is measured before blood storage is begun, then from the change in its volume it is possible to know the amount of change in the volume of the blood storage chamber 1. The change in the volume of the volume adjustment chamber 2 can be measured from the change in the amount of volume adjustment liquid that is accommodated by the adjustment liquid reservoir 21.

The extracorporeal blood circulation method with this extracorporeal blood circulation apparatus is described with reference to FIGS. 9 through 14. It should be noted that for the sake of ease in understanding, FIGS. 9 through 14 show the closed-type blood reservoir 20 in cross section. Thus, for the sake of illustration, the blood inlet port 4 and the blood outlet port 5 are depicted by imaginary lines. Further, when performing extracorporeal blood circulation, other apparatuses such as an oxygenator and a blood filter also are connected to the circulation route, but these are not shown in the drawings.

Figure 9:
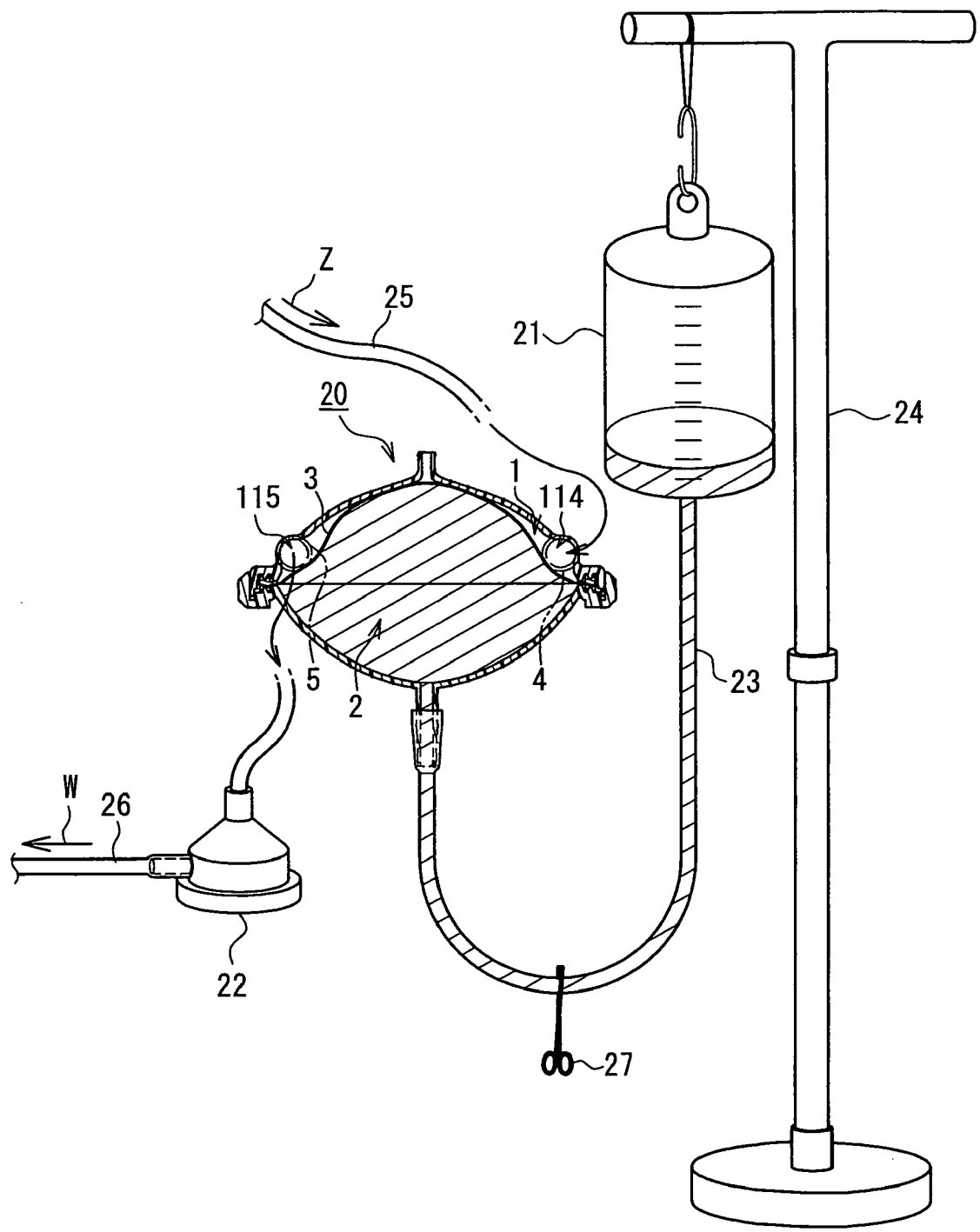
FIG. 9 is a schematic view illustrating the operation of the extracorporeal blood circulation apparatus of Embodiment 4 prior to the start of extracorporeal blood circulation.

First, the steps and the operation prior to the start of extracorporeal blood circulation, that is, the steps and the operation of priming prior to the start of extracorporeal blood circulation, are described with reference to FIG. 9. When using the closed-type blood reservoir 20, an appropriate amount of saline solution or the like is filled as an adjustment liquid into the system including the volume adjustment chamber 2, the tube 23, and the adjustment liquid reservoir 21, to set the blood storage volume of the blood storage chamber 1 to a size that is appropriate for priming. Specifically, the adjustment liquid reservoir 21 is raised to a high position and the volume adjustment liquid is filled sufficiently into the volume adjustment chamber 2, moving the septum 3 toward the inner surface of the outer shell in opposition to the blood storage chamber 1 so as to adjust the volume of the blood storage chamber 1 such that a minimum flow route, that is, the flow route cross-sectional area that is required for subsequent priming, is secured. In this state, the adjustment liquid route tube 23 is closed off by forceps 27. The priming liquid is filled into this extracorporeal blood circulation system, which includes a blood storage chamber 3 that functions at the minimum volume that has been formed in this manner. Priming is performed by driving the blood pump.

Figure 10:
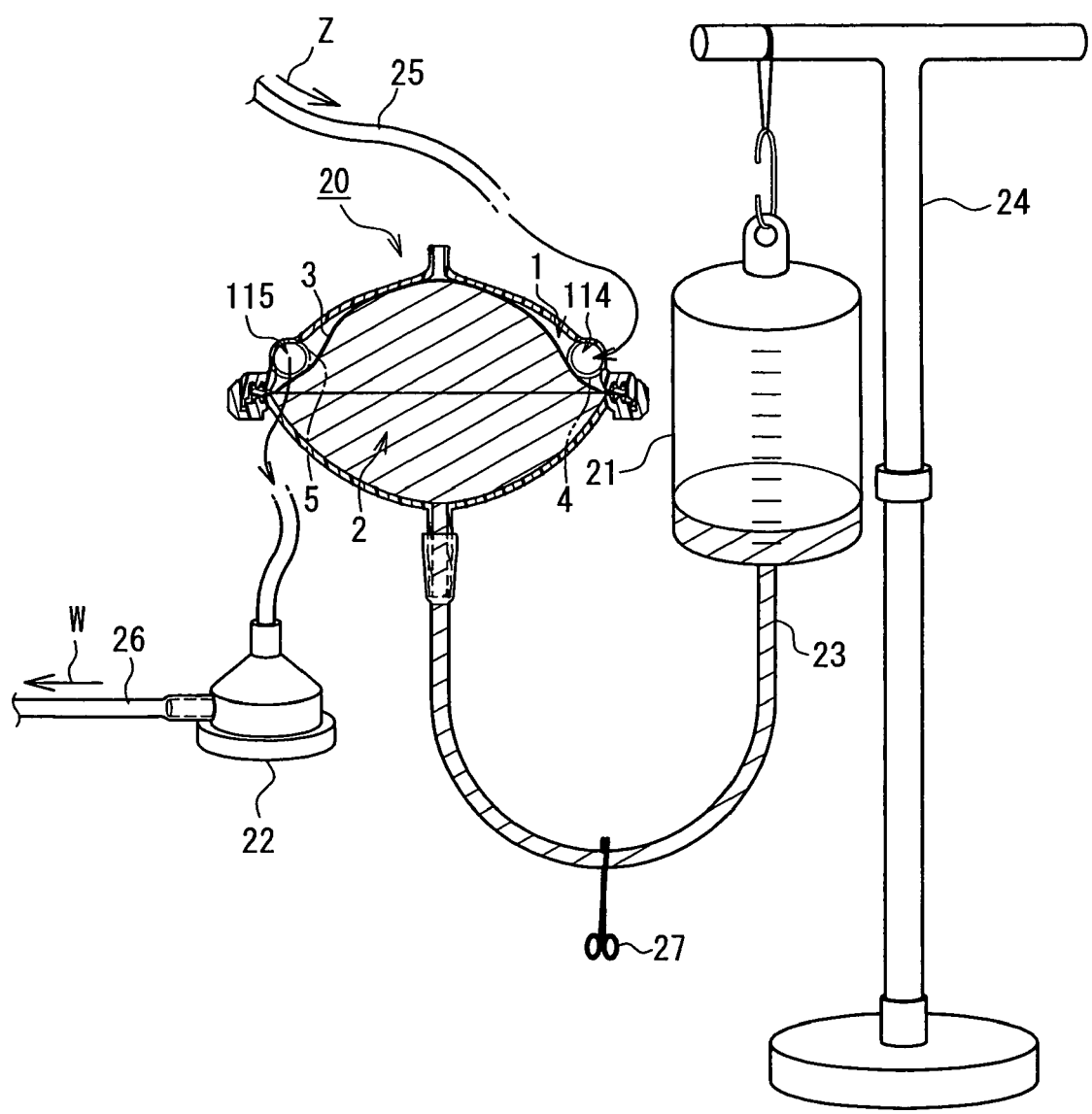
FIG. 10 is a schematic view illustrating the operation of the extracorporeal blood circulation apparatus of Embodiment 4 when extracorporeal blood circulation is started.

Next, the steps and the operation at the start of extracorporeal blood circulation are described with reference to FIG. 10. After priming is finished, the adjustment liquid reservoir 21 is lowered to a lower position with respect to the closed-type blood reservoir 20 than in the case of FIG. 9. When operation of the blood pump 22 is started while maintaining this state, the blood removal operation is started, and extracorporeal blood circulation is started.

Figure 11:
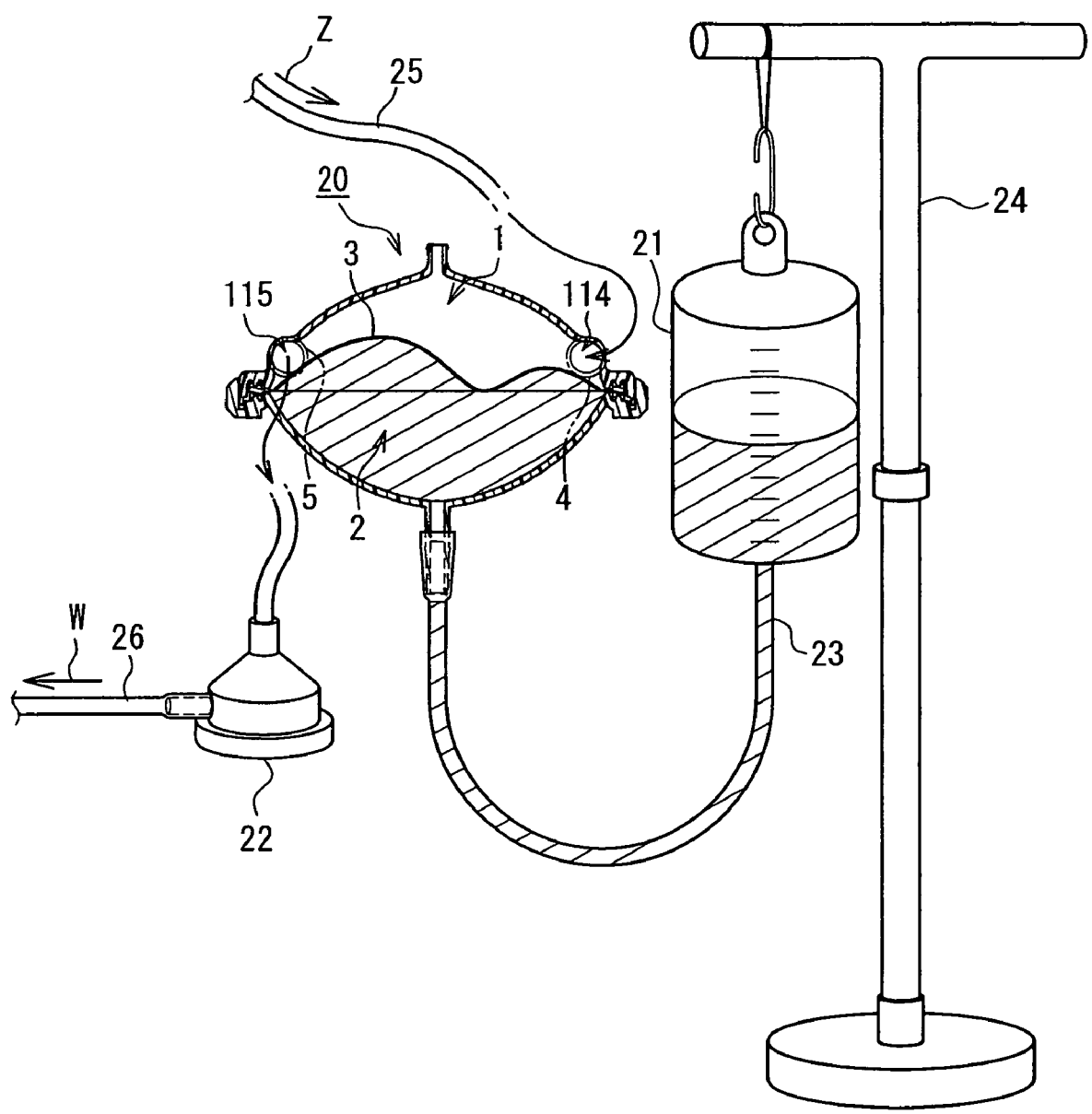
FIG. 11 is a schematic view illustrating the operation of the extracorporeal blood circulation apparatus of Embodiment 4 at the start of and during blood withdrawal.

Next, the steps and the operation at the start of and during blood removal are described with reference to FIG. 11. When the forceps 27 are removed from the state shown in FIG. 10, the pressure from the level difference between the site where blood is removed from the body and the adjustment liquid reservoir 21 makes it possible for the adjustment liquid to move from the volume adjustment chamber 2 to the adjustment liquid reservoir 21. As a result, blood is removed from the body, and the blood that flows into the blood storage chamber 1 causes the septum 3 to move toward the volume adjustment chamber 2, increasing the volume of the blood storage chamber 1. During extracorporeal blood circulation, the position of the septum 3 varies according to the internal pressure of the extracorporeal blood circulation system, and the volume of the blood storage chamber 1 is adjusted automatically. The height of the volume adjustment chamber 2 is set according to the estimated pressure of the blood in the extracorporeal blood circulation system and the target volume for the blood storage chamber 1, but it is also possible for the height to be adjusted suitably during extracorporeal blood circulation.

Figure 12A:
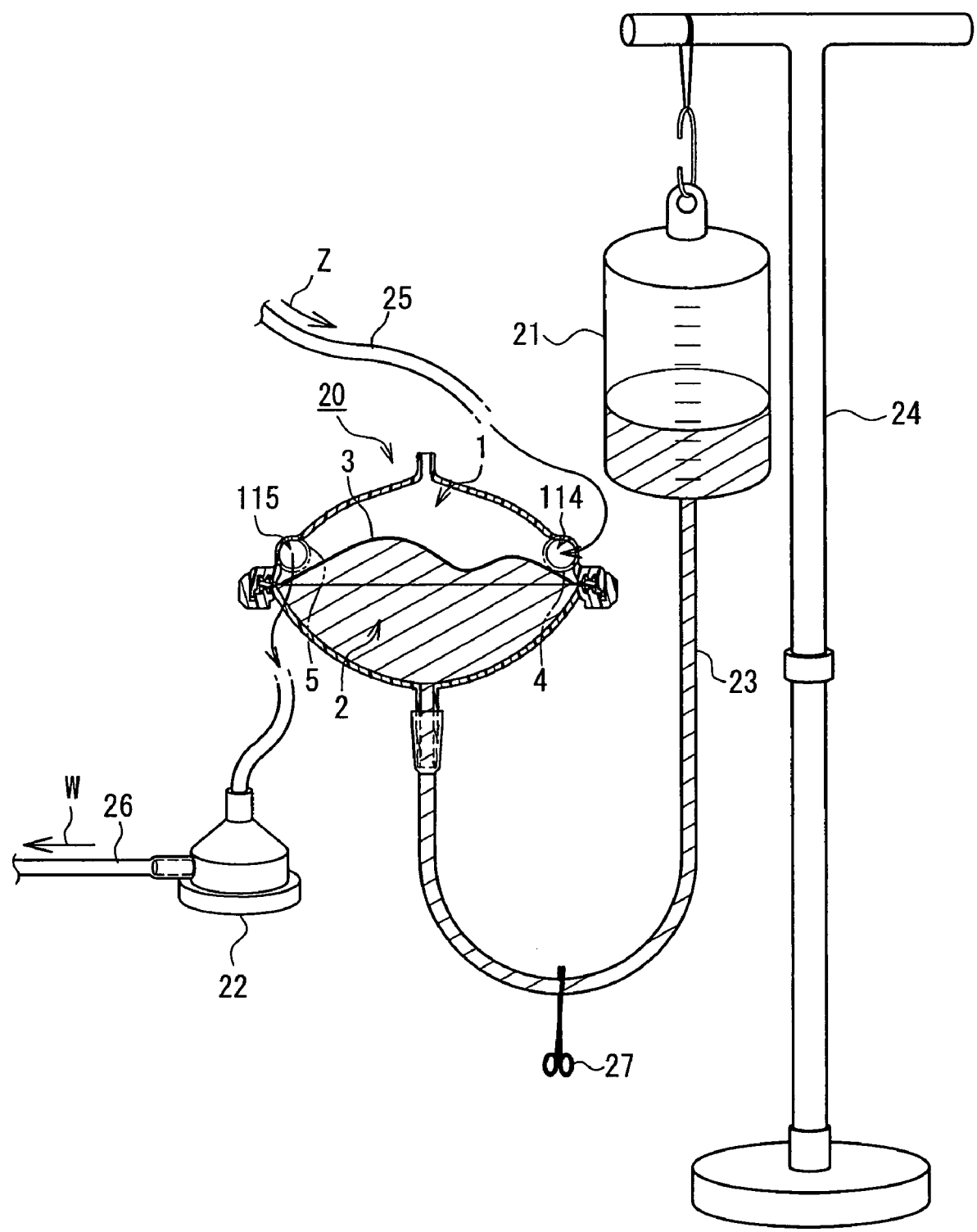
FIG. 12A is a schematic view illustrating an example of the operation of the extracorporeal blood circulation apparatus of Embodiment 4 when increasing the blood amount of the heart.
Figure 12B:
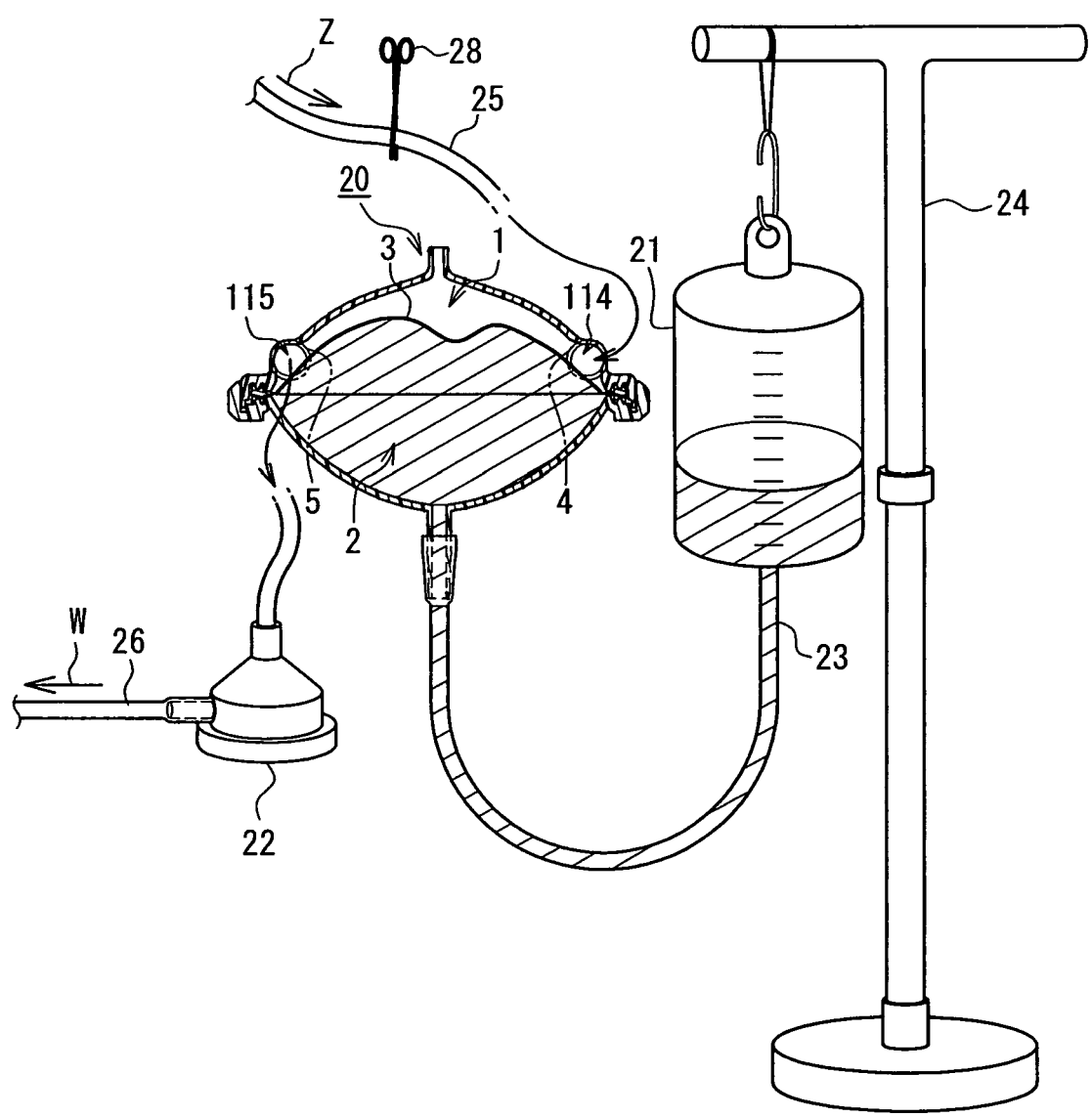
FIG. 12B is a schematic view illustrating another example of the operation of the extracorporeal blood circulation apparatus of Embodiment 4 when increasing the blood amount of the heart.

Next, the adjustment procedure for increasing the amount of blood in the heart of the body is described with reference to FIGS. 12A and 12B. FIGS. 12A and 12B each describe a different adjustment procedure. If the blood-removal tube becomes adhered at the site where blood is removed from the body, then the following adjustment procedure can be performed to increase the amount of blood in the heart and thereby eliminate adherence of the blood-removal tube.

In the first adjustment procedure, first, in a state where the forceps 27 is not being used, the position of the adjustment liquid reservoir 21 is raised to send adjustment liquid to the volume adjustment chamber 2. The septum 3 moves toward the blood storage chamber 1 in accordance with the amount of adjustment liquid that has been sent, and the volume of the blood storage chamber 1 decreases. As a result, the blood that is stored in the blood storage chamber 1 is ejected from the blood reservoir 20 and returns to the body, increasing the amount of blood in the heart. When the blood storage chamber 1 has been set to an appropriate volume, the forceps 27 are used to close off the adjustment liquid route tube 23 and keep that state (see FIG. 12A).

In the second adjustment procedure, first, part of the blood-removal side tube 25 is narrowed by forceps 28. By doing this, the blood storage chamber 1 pressure drops and adjustment liquid is sent to the volume adjustment chamber 2 from the adjustment liquid reservoir 21. The septum 3 moves toward the blood storage chamber 1 in correspondence with the amount of adjustment liquid that has been sent to the volume adjustment chamber 2, reducing the volume of the blood storage chamber 1. As a result, the blood that is stored in the blood storage chamber 1 is discharged from the blood reservoir 20 and returns to the body, increasing the blood volume of the heart. When the blood storage chamber 1 has been set to an appropriate volume, forceps are used to close off the adjustment liquid route tube 23 and maintain that state (see FIG. 12B).

Figure 13:
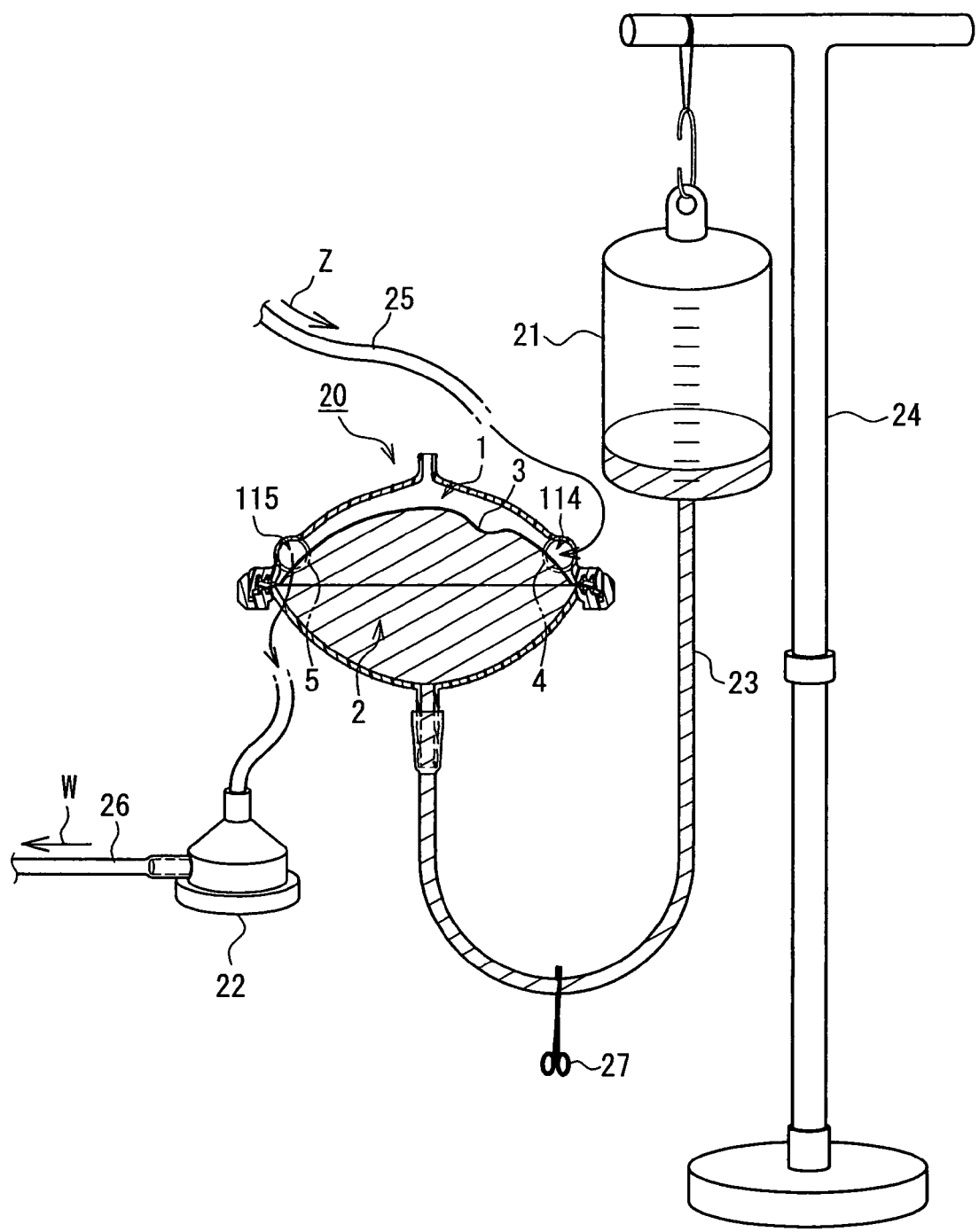
FIG. 13 is a schematic view illustrating the operation when ending extracorporeal blood circulation using the extracorporeal blood circulation apparatus of Embodiment 4.

Lastly, the procedure and the operation when leaving the state of extracorporeal blood circulation are described with reference to FIG. 13. First, the position of the adjustment liquid reservoir 21 is raised in order to reduce the amount that is sucked in by the blood pump 22. By doing this, the adjustment liquid moves from the adjustment liquid reservoir 21 to the volume adjustment chamber 2 and the septum 3 moves toward the blood storage chamber 1, reducing the volume of the blood storage chamber 1. In this state, extracorporeal blood circulation is ended after the adjustment liquid route tube 23 has been blocked off by the forceps 27.

Figure 14:
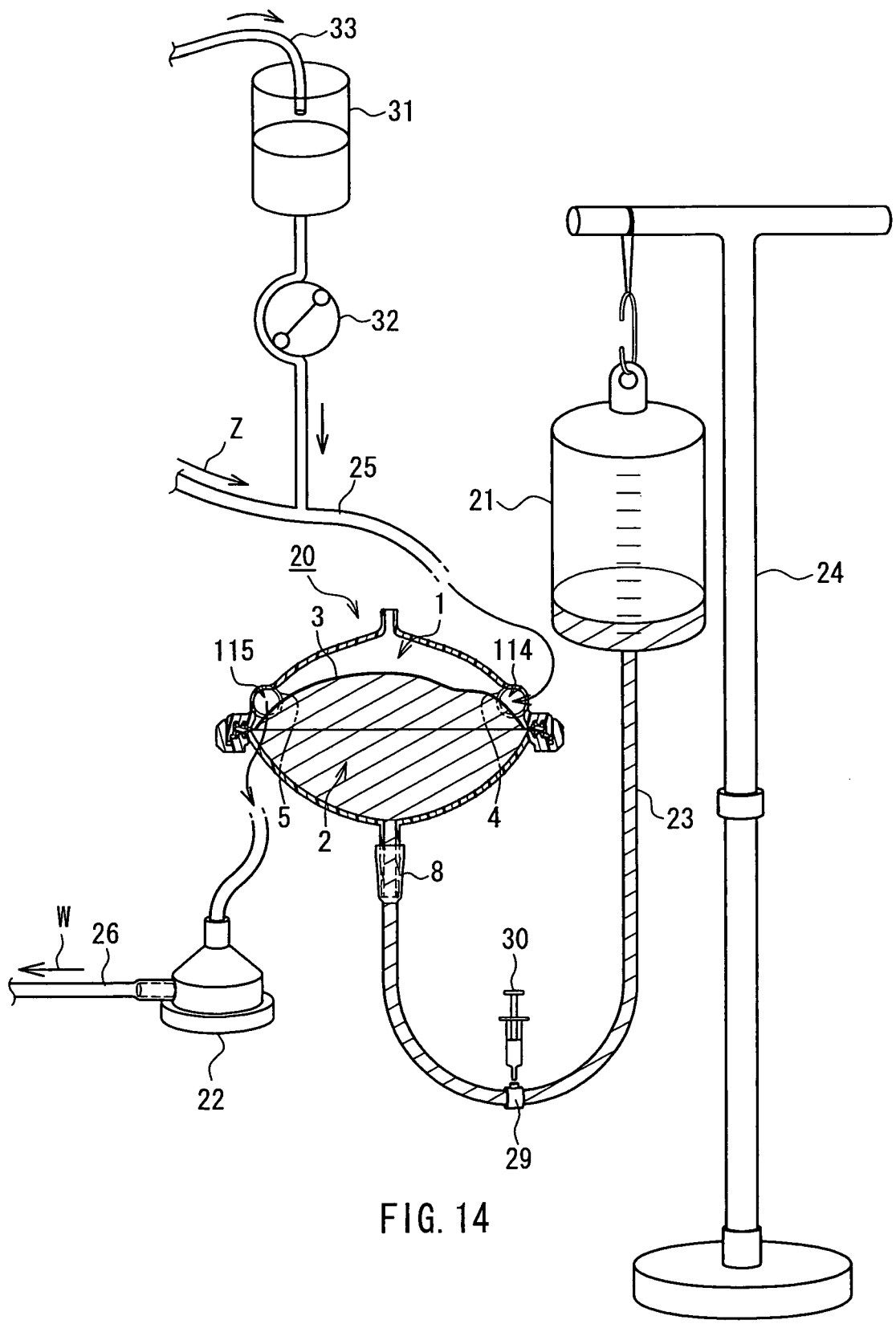
FIG. 14 is a schematic view showing another example of the extracorporeal blood circulation apparatus of Embodiment 4.

FIG. 14 is a perspective view showing an extracorporeal blood circulation apparatus in which additional elements have been added to the extracorporeal blood circulation apparatus having the above configuration.

The first additional element is a fine-tune port 29 that is provided in the adjustment liquid route tube 23. Through the fine-tune port 29 it is possible to inject and discharge adjustment liquid with a syringe 30, and by doing so the amount of adjustment liquid that is filled into the volume adjustment chamber 2 can be fine tuned.

A second additional element is an auxiliary circulation system made from an auxiliary blood reservoir 31 and a pump 32. The auxiliary blood reservoir 31 is shown simplistically, but it is a general open-type blood reservoir. An auxiliary system tube 33 for recovering blood lost from other than the site where blood is removed from the body is connected to the auxiliary blood reservoir 31. The auxiliary blood reservoir 31 is connected to the blood inlet port 4 of the closed-type blood reservoir 20 via the pump 32, and supplies the closed-type blood reservoir 20 with blood that has collected in the auxiliary blood reservoir 31.

The extracorporeal blood circulation apparatus of this embodiment is designed such that by changing the height of the adjustment liquid reservoir 21, the adjustment liquid flows in and out due to the change in the height difference, but the extracorporeal blood circulation apparatus of this embodiment may also be configured such that adjustment liquid is moved in and out of the volume adjustment chamber 2 from the adjustment liquid reservoir 21 by a pump.

The volume adjustment chamber 2 is separated from the blood storage chamber 1 by the septum 3, and thus the blood will not become contaminated. Consequently, it is not necessary specifically to use a sterilized adjustment liquid to serve as the adjustment liquid that is filled into the volume adjustment chamber 2, but it is desirable for a sterilized isotonic liquid such as saline solution to be used in case the septum 3 breaks.

Embodiment 5

In Embodiment 5, an example of a second closed-type blood reservoir of the invention, an example of a third closed-type blood reservoir of the invention, and second and third extracorporeal blood circulation apparatuses of the invention that employ these, are described.

Figure 16:
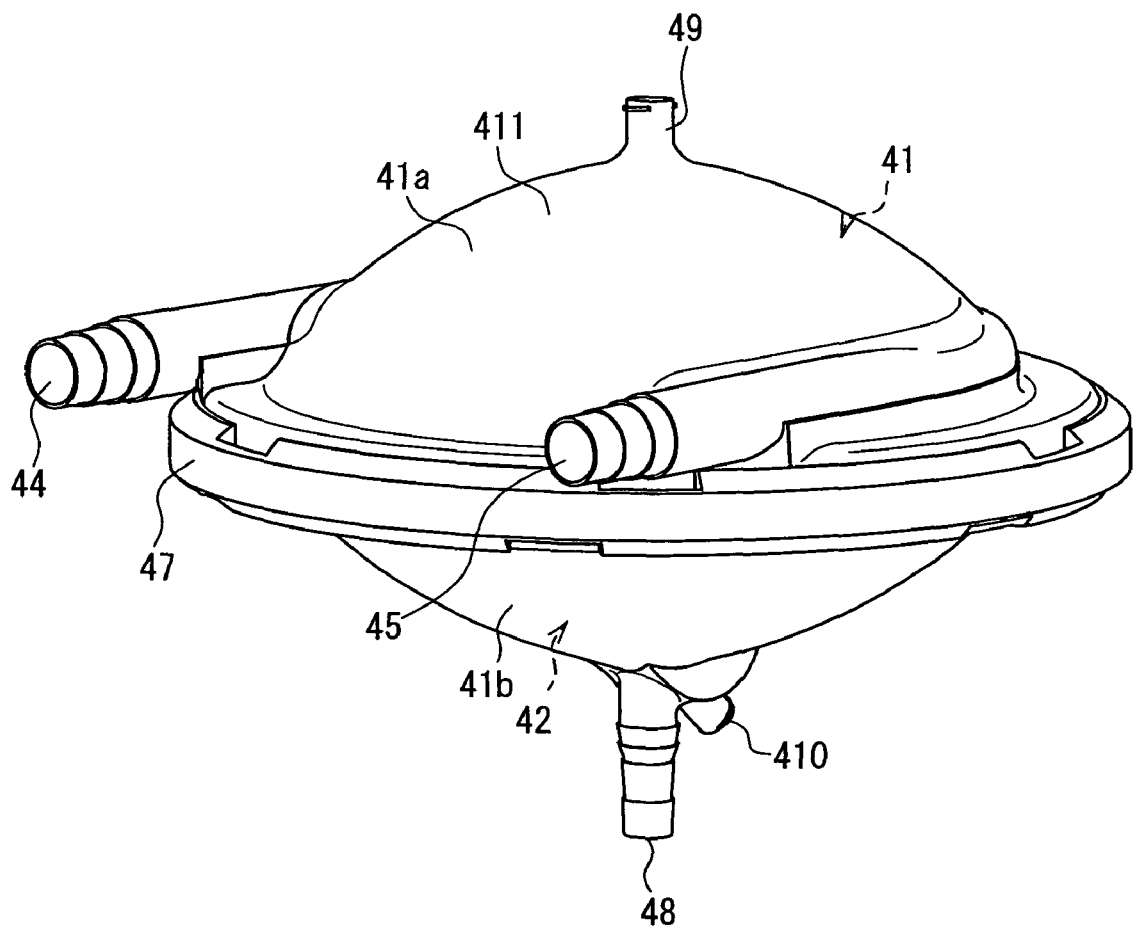
FIG. 16 is a perspective view showing an example of the closed-type blood reservoir of Embodiment 5.
Figure 17:
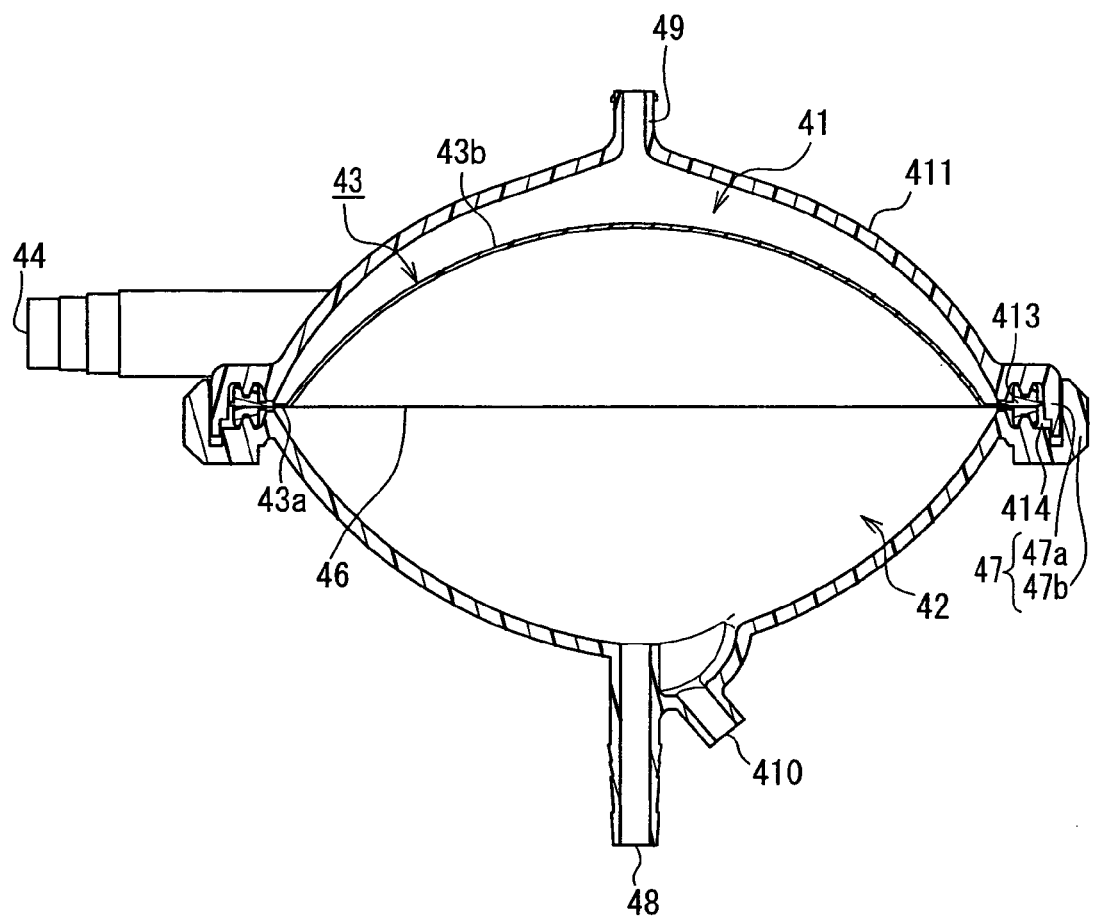
FIG. 17 is a cross-sectional diagram of the closed-type blood reservoir shown in FIG. 16.

FIG. 16 is a perspective view of an example of a closed-type blood reservoir of this embodiment, and FIG. 17 is a cross-sectional view of a front view thereof. With the closed-type blood reservoir of this embodiment that is shown in FIGS. 16 and 17, a blood inlet port 44 and a blood outlet port 45 are disposed in opposite positions compared to those of the closed-type blood reservoir of Embodiment 1.

As shown in FIG. 16, this blood reservoir has a housing that is formed by an outer shell that results from the joining of a blood storage chamber shell 41a, which has a curved surface that is outwardly convex, and a volume adjustment chamber shell 41b, which has a curved surface that is outwardly convex, at a joining portion 47. The blood storage chamber shell 41a is provided with a blood inlet port 44, a blood outlet port 45, and a blood storage chamber air discharge port 49. The volume adjustment chamber shell 41b is provided with a volume adjustment liquid port 48 and a volume adjustment chamber air discharge port 410.

As shown in FIG. 17, the blood storage chamber shell 41a and the volume adjustment chamber shell 41b are in close contact with one another at a contact face 46, forming a space in their interior. A flexible septum 43 is interposed between the blood storage chamber shell 41a and the volume adjustment chamber shell 41b and divides the internal space into a blood storage chamber 41 for temporarily storing blood and a volume adjustment chamber 42 for storing volume adjustment liquid. The blood inlet port 44 and the blood outlet port 45 are used for blood to flow into and away from the blood storage chamber 41. The blood storage chamber air discharge port 49 is provided for the purpose of discharging air bubbles that have become mixed in with the blood that is introduced into the blood storage chamber 41. The volume adjustment liquid port 48 is used for injecting and ejecting volume adjustment liquid into and from the volume adjustment chamber 42.

The septum 43 has the shape shown in FIG. 17, and is provided with a peripheral flat portion 43a and an inner curved portion 43b. The flat portion 43a is a section where part of the region on the inner side of the outer circumferential edge of the blood storage chamber shell 41a has a substantially flat shape. A circular retaining member 413 that is provided outside the circular flat portion 43a is sandwiched between the blood storage chamber shell 41a and the volume adjustment chamber shell 41b, and thus the septum 43 is supported by the outer shell 411. A gap 414 is formed by the joining of a first joining portion 47a of the blood storage chamber shell 41a and a second joining portion 47b of the volume adjustment chamber shell 41b, and the retaining member 413 either is formed in a single unit with the septum 43 or is fastened to the septum 43, and engages the gap 414.

The inner surface of the blood storage chamber shell 41a has a shape defined by a rotated circular arc surface. The curved portion 43b of the septum 43 is shown in FIG. 17 to bulge toward the blood storage chamber shell 41a, but it is formed such that it can project outward in a curved shape toward the blood storage chamber shell 41a or the volume adjustment chamber shell 41b. The curvature of the molded shape of the curved portion 43b of the septum 43 is smaller than the curvature of the inner surface of the blood storage chamber shell 41a. FIG. 17 shows the shape of the septum 43 in a state where it is not substantially deformed and retains its molded shape. In practice, because the septum 43 is flexible, in some cases it may not be able to keep the shape that is shown in drawing. Thus, the curvature of the curved portion 43b is defined in a state where the molded shape is retained.

Figure 18:
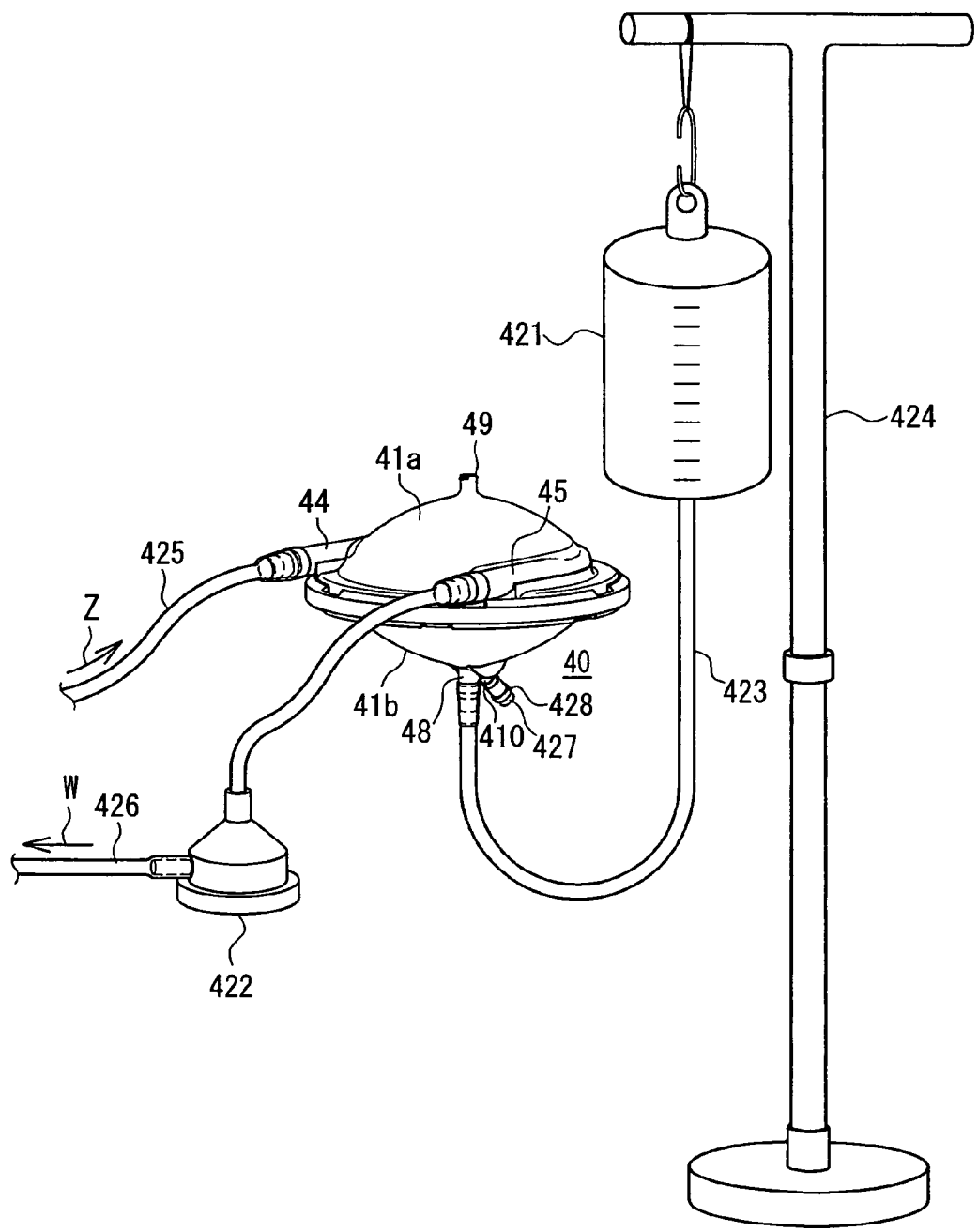
FIG. 18 is a perspective view showing an example of an extracorporeal blood circulation apparatus using the closed-type blood reservoir shown in FIG. 16.

The blood reservoir is for example used as shown in FIG. 18. FIG. 18 shows the configuration of an extracorporeal blood circulation apparatus that is formed using a closed-type blood reservoir that has a structure like that discussed above. This extracorporeal blood circulation apparatus is provided with a closed-type blood reservoir 40 with the above configuration, a volume adjustment liquid reservoir 421, and a blood pump 422 made from a centrifugal pump, for example. The closed-type blood reservoir 40 is disposed such that the blood storage chamber shell 41a is above and the volume adjustment chamber shell 41b is below.

The adjustment liquid reservoir 421 is connected to the volume adjustment liquid port 48 of the closed-type blood reservoir 40 by a flexible adjustment liquid route tube 423 that is a conduit member. An air discharge tube 427 is connected to the volume adjustment chamber air discharge port 410, and is narrowed by and blocked off by the forceps 428. The inlet opening of the blood pump 422 is connected to the blood outlet port 45 of the closed-type blood reservoir 40. The volume adjustment liquid reservoir 421 is supported by a support fitting 424 that allows its height relative to the closed-type blood reservoir 40 to be adjusted. A flexible blood-removal side tube 425 that is connected to the site where blood is withdrawn from the body is connected to the blood inlet port 44 of the closed-type blood reservoir 40, and blood flows in as shown by the arrow Z. A flexible blood-return side tube 426 that is connected to the site where blood is returned is connected to the ejection opening of the blood pump 422, and blood flows out as shown by the arrow W.

The adjustment liquid reservoir 421 has the function of storing the volume adjustment liquid that is injected to and discharged from the volume adjustment chamber 42 of the closed-type blood reservoir 40 (see FIG. 17). The adjustment liquid route tube 423 is for example constituted by a tube that is flexible, and by narrowing the tube with forceps it is possible to block, open, or partially block the flow route, allowing the flow route cross-sectional area to be changed. It is also possible to adopt a structure in which the adjustment liquid route tube 423 has a flow route adjustment member for changing the flow route cross-sectional area, such as a cock, within its flow route.

The adjustment liquid reservoir 421 also has a measurement portion, such as a scale, for measuring the amount of volume adjustment liquid that is being stored.

By changing the position where the support fitting 424 supports the volume adjustment liquid reservoir 421 in order to adjust the height of the adjustment liquid reservoir 421 with respect to the site where blood is withdrawn from the body, that is, to adjust the height difference of the volume adjustment liquid, it is possible to increase or decrease the amount of volume adjustment liquid that is stored in the volume adjustment chamber 42. Thus, the volume of the blood storage chamber 41 is adjusted by moving the septum 43. As long as the capacity of the volume adjustment chamber 42 is measured before the start of blood storage, then from the change in its volume it is possible to know the amount of change in the volume of the blood storage chamber 41. The change in the volume of the volume adjustment chamber 42 can be measured from the change in the amount of volume adjustment liquid that is accommodated within the volume adjustment liquid reservoir 421.

The blood reservoir of this embodiment has a structure like that described in reference to FIGS. 16 and 17, and is used in an extracorporeal blood circulation apparatus such as that shown in FIG. 18. At this time, the septum 43 has a flat portion 43a at its periphery such that the curved portion 43b of the septum 43 is raised up from the inner surface of the blood storage chamber shell 41a, such as from a position removed inward by the dimensions of the flat portion 43a. Thus, at the circumferential edge portion of the septum 43, a space with predetermined dimensions and shape is secured in the area between this portion and the inner surface of the blood storage chamber shell 41a. In other words, as long as the volume adjustment liquid is injected into the volume adjustment chamber 42 at the normal usage pressure, then the molded shape shown in FIG. 17 is maintained, with the septum 43 bulging maximally toward the blood storage chamber shell 41a. Consequently, at a minimum, a space such as that shown in FIG. 17 is secured as the blood storage chamber 41. As a result, the blood outlet port 45 is kept from being blocked off by the septum 43, and the blood outlet port 45 always can be kept open within the blood storage chamber 41 without providing the first blood flow route 114 in the blood storage chamber as in the blood reservoir of Embodiment 1. The risk that the task of filling in the priming liquid while preparing for use is hindered, and that some of the circulation liquid will collect in the blood storage chamber 41 and become the source of blood clots forming in the blood is reduced. Further, blood can be recovered efficiently from within the blood reservoir when the extracorporeal blood circulation has finished.

By keeping the retaining member 413 between the blood storage chamber shell 41a and the volume adjustment chamber shell 41b, also it becomes possible to fasten the septum 43 readily. To position the septum 43 when the blood storage chamber shell 41a and the volume adjustment chamber shell 41b are joined, it is sufficient to position the retaining member 413 with respect to the blood storage chamber 41 and the volume adjustment chamber shell 41b. Further, since the septum 43 is provided with the flat portion 43a, there is a large leeway in the positioning precision, and this makes the assembly process easy.

In an example of the third blood reservoir of the invention, as discussed above it is preferable that the curved portion 43b of the septum 43 has a smaller curvature than the curvature of the inner surface of the blood storage chamber shell 41a. In such a case, as shown in FIG. 17, a space having predetermined dimensions and shape is secured between the inner surface of the blood storage chamber shell 41a and the septum 43, making it possible to further ensure the above-described effect. In this case, it is possible to obtain a dimensional relationship in which the spacing between the blood storage chamber shell 41a and the septum 43 is largest at the center portion and becomes smaller with increased proximity to the peripheral portion, and thus when the septum moves along with variations in the stored blood volume, the blood storage chamber shell 41a and the septum 43 start to draw closer to one another starting from the peripheral portion and progressing toward the center portion.

It should be noted that even if the septum 43 is not provided with the flat portion 43a, as long as the curved portion 43b of the septum 43 has a smaller curvature than the curvature of the inner surface of the blood storage chamber shell 41a, then the blood outlet port 45 is kept from being blocked off by the septum 43.

The above characteristic allows air bubbles that stay near the peripheral portion of the blood storage chamber to be removed easily when performing the task of filling in priming liquid during preparation for use.

The operation of the extracorporeal blood circulation apparatus using this closed-type blood reservoir is described below with reference to FIGS. 17 and 18. When this blood reservoir is used, first priming is performed. At this time, unlike in the illustration of FIG. 18, the closed-type blood reservoir 40 is disposed such that the volume adjustment chamber shell 41b is above and the blood storage chamber shell 41a is below. The volume adjustment liquid (such as saline solution) is injected into the volume adjustment chamber 42 from the volume adjustment liquid reservoir 421. The injection of saline solution is performed until the septum 43 is maximally distended toward the inner surface of the blood storage chamber shell 41a. Next, priming liquid is filled into the extracorporeal blood circulation route, which includes the blood storage chamber 41.

After priming is complete, the closed-type blood reservoir 40 is flipped over to attain the state shown in FIG. 18. When extracorporeal blood circulation is started, the blood that has been removed from the body is introduced into the blood storage chamber 41 through the blood inlet port 44, and is discharged from the blood storage chamber 41 through the blood outlet port 45. At this time, when the height of the volume adjustment liquid reservoir 421 is adjusted so that the saline solution of the volume adjustment chamber 42 is ejected into the volume adjustment liquid reservoir 421, the septum 43 moves in accordance with the amount of saline solution that is ejected from the volume adjustment chamber 42, increasing the volume of the blood storage chamber 41. In other words, an amount of blood that corresponds to the amount of saline solution that has been transferred to the volume adjustment liquid reservoir 421 becomes stored in the blood storage chamber 41. That amount can be ascertained reliably from the volume adjustment liquid reservoir 421.

Conversely, when the volume adjustment liquid reservoir 421 is raised in height in order to send saline solution to the volume adjustment chamber 42, the septum 43 moves toward in the blood storage chamber 41 according to that amount of saline solution and reduces the volume of the blood storage chamber 41. As a result, the blood that is stored in the blood storage chamber 41 is discharged from the blood reservoir and consequently is returned to the body. That amount can be ascertained reliably from the volume adjustment liquid reservoir 421.

As illustrated above, the volume of the blood storage chamber 41 can be changed with ease, and, moreover, the volume of the changed blood storage chamber 41, that is, the stored blood volume, can be readily ascertained. Consequently, in extracorporeal blood circulation it is not necessary to select a blood reservoir with an appropriate volume each time based on patient conditions, and by preparing a blood reservoir with a certain degree of volume it is possible to handle small to large volumes.

The volume adjustment chamber 42 is separated from the blood storage chamber 41 by the septum 43, and thus the blood will not become contaminated. Consequently, it is not necessary specifically to use a sterilized adjustment liquid as the adjustment liquid that is loaded into the volume adjustment chamber 42, but it is desirable for a sterilized isotonic liquid such as saline solution to be used in case the septum 43 breaks.

The materials making up the blood storage chamber shell 41a and the volume adjustment chamber shell 41b can be the same as those materials in the blood reservoir of Embodiment 1. The material for the septum 43 also can be the same as the material of the septum in the blood reservoir of Embodiment 1.

Embodiment 6

In Embodiment 6, an example of a fourth closed-type blood reservoir of the invention, and an example of a fourth extracorporeal blood circulation apparatus of the invention, are described.

Figure 19:
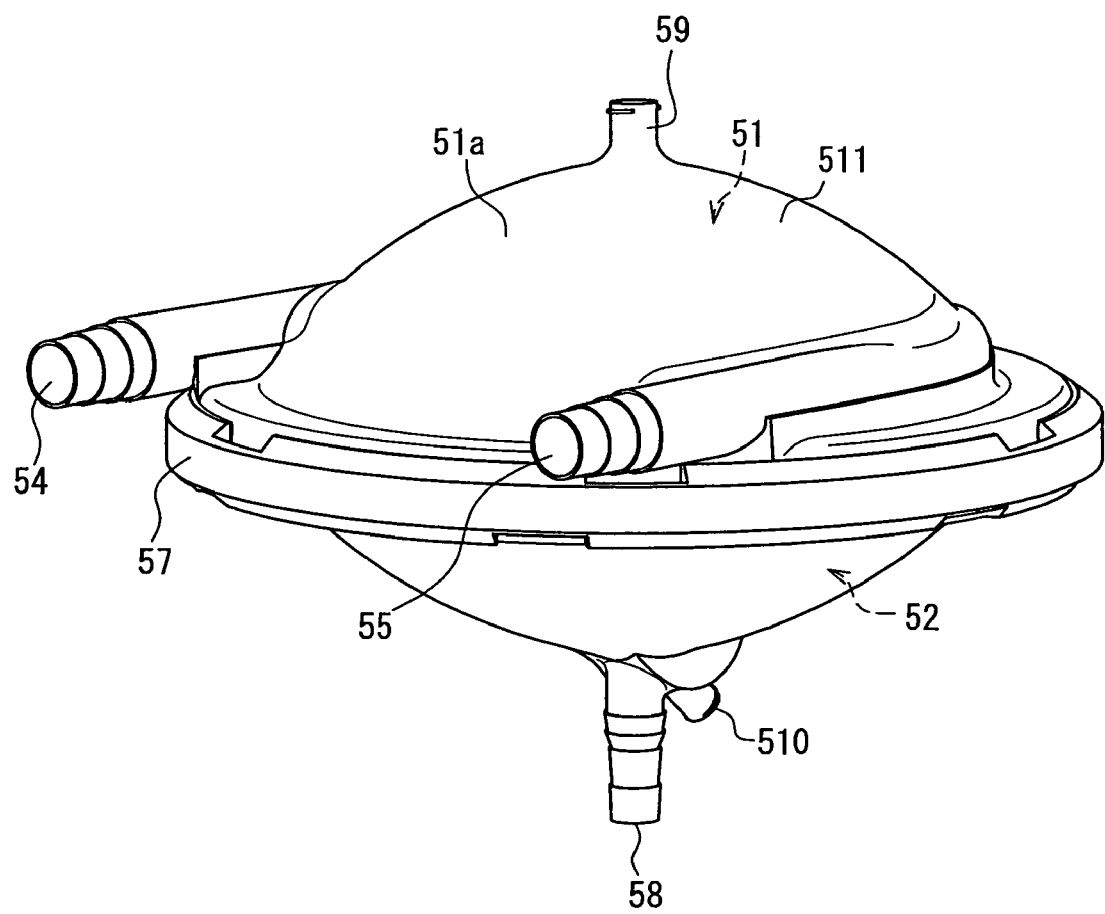
FIG. 19 is a perspective view showing an example of the closed-type blood reservoir of Embodiment 6.
Figure 20:
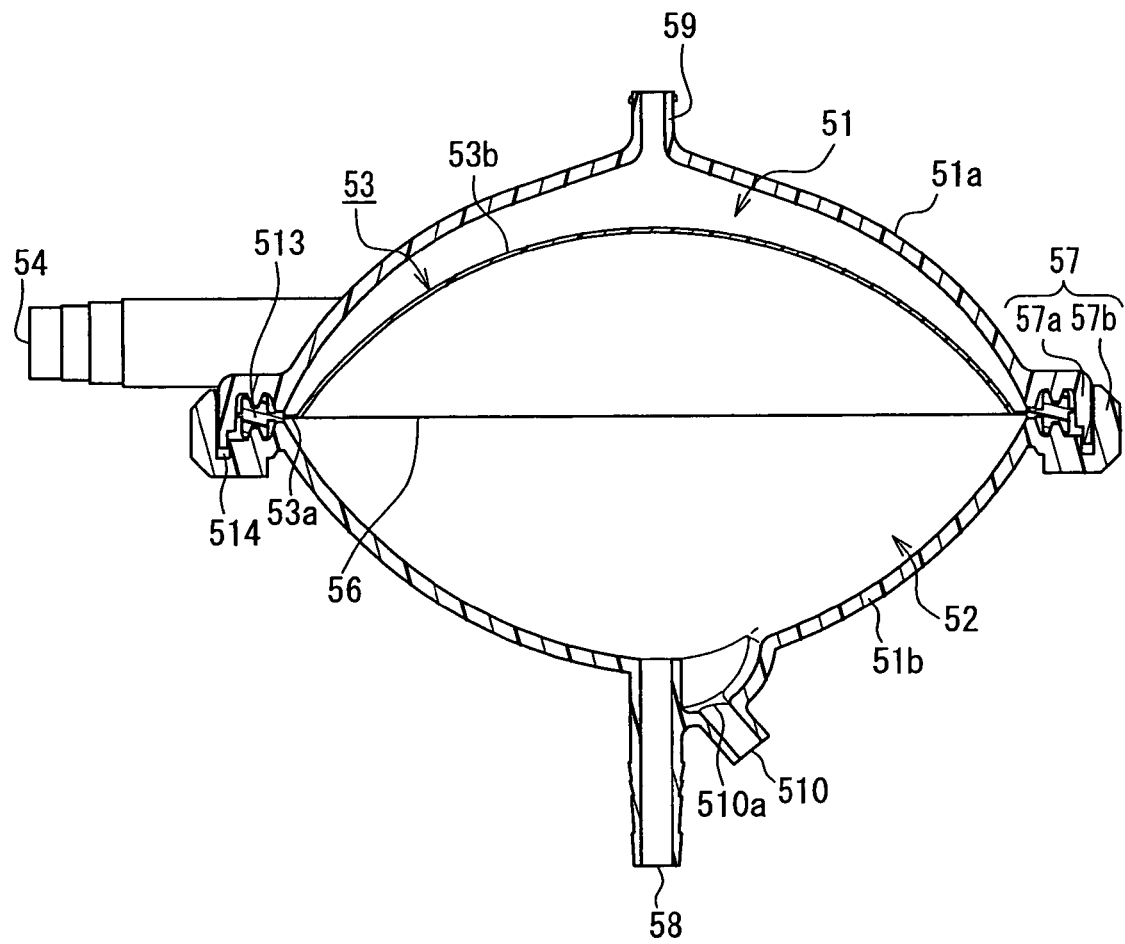
FIG. 20 is a cross-sectional diagram of the closed-type blood reservoir shown in FIG. 19.

FIG. 19 is a perspective view showing the closed-type blood reservoir of this embodiment, and FIG. 20 is a cross-sectional view of a front view of the same.

As shown in FIG. 19, the blood reservoir has a housing that is formed by an outer shell 511 that is formed by the joining of a blood storage chamber shell 51a, which has a curved surface that is outwardly convex, and a volume adjustment chamber shell 51b, which also has a curved surface that is outwardly convex, at a joining portion 57. The blood storage chamber shell 51a is provided with a blood inlet port 54, a blood outlet port 55, and a blood storage chamber air discharge port 59. The volume adjustment chamber shell 51b is provided with a volume adjustment liquid port 58 and a volume adjustment chamber air discharge port 510.

As shown in FIG. 20, the blood storage chamber shell 51a and the volume adjustment chamber shell 51b are in close contact with one another at a junction face 56, forming a space in their interior. A flexible septum 53 is interposed between the blood storage chamber shell 51a and the volume adjustment chamber shell 51b and divides that internal space into a blood storage chamber 51 for temporarily storing blood and a volume adjustment chamber 52 for storing the volume adjustment liquid. The blood inlet port 54 and the blood outlet port 55 are used for allowing blood to flow into or away from the blood storage chamber 51. The blood storage chamber air discharge port 59 is provided for the purpose of discharging air bubbles that have become mixed in with the blood that flows into the blood storage chamber 51. The volume adjustment liquid port 58 is used for introducing and discharging volume adjustment liquid into and from the volume adjustment chamber 52. The volume adjustment chamber air discharge port 510 is provided for the purpose of discharging air bubbles that remain in the volume adjustment chamber 52 during priming.

The septum 53 has the shape shown in FIG. 20, and includes a peripheral flat portion 53a and an inner curved portion 53b. The flat portion 53a is a section where some of the region on the inner side of the blood storage chamber shell 51a along its outer circumferential edge has a substantially flat shape. A retaining member 513 that is provided outside the flat portion 53a is sandwiched between the blood storage chamber shell 51a and the volume adjustment chamber shell 51b and thus the septum 53 is retained on the outer shell 511. In other words, by having the retaining member 513 either formed in a single unit with the flat portion 53a or fastened to the flat portion 53a be supported in the space 514 within the joining portion 57, the septum 53 is fastened to the outer shell. The gap 514 is formed by the joining of a first joining portion 57a of the blood storage chamber shell 51a and a second joining portion 57b of the volume adjustment chamber shell 51b, and the retaining member 513 engages with the gap 414.

The inner surface of the blood storage chamber shell 51a has a shape of a rotated circular arc surface. The curved portion 53b of the septum 53 is formed bulging toward the blood storage chamber shell 51a, and the curvature of the molded shape is smaller than the curvature of the inner surface of the blood storage chamber shell 51a. FIG. 20 shows the shape of the septum 53 in a state where it is not substantially deformed and it retains its molded shape. It shows the shape of the septum 53 in a state where it is not substantially deformed and it retains its molded shape. In practice, because the septum 53 is flexible, in some cases it may not be able to retain the shape that is shown in drawing. Consequently, the curvature of the curved portion 53b is defined in the state in which the molded shape is retained.

As shown in FIG. 20, the volume adjustment chamber shell 51b has a shape in which its center portion forms an apex. The volume adjustment liquid port 58 is provided in the center portion of the volume adjustment chamber shell 51b, and the volume adjustment chamber air discharge port 510 is provided adjacent to the volume adjustment liquid port 58. The tip of the volume adjustment liquid port 58 is formed to be located farther from the outer wall surface of the volume adjustment chamber shell 51b than the tip of the volume adjustment chamber air discharge port 510. By providing the volume adjustment chamber air discharge port 510, an air discharge port opening 510a that is formed in the volume adjustment chamber shell 51b is disposed in the middle of the depression that is provided from the inner wall surface of the volume adjustment chamber shell 51b toward the outside. It should be noted that, although not shown, a tube is connected to the volume adjustment chamber air discharge port 510, and disposing an air filter in that tube is favorable for maintaining sterility.

Figure 21:
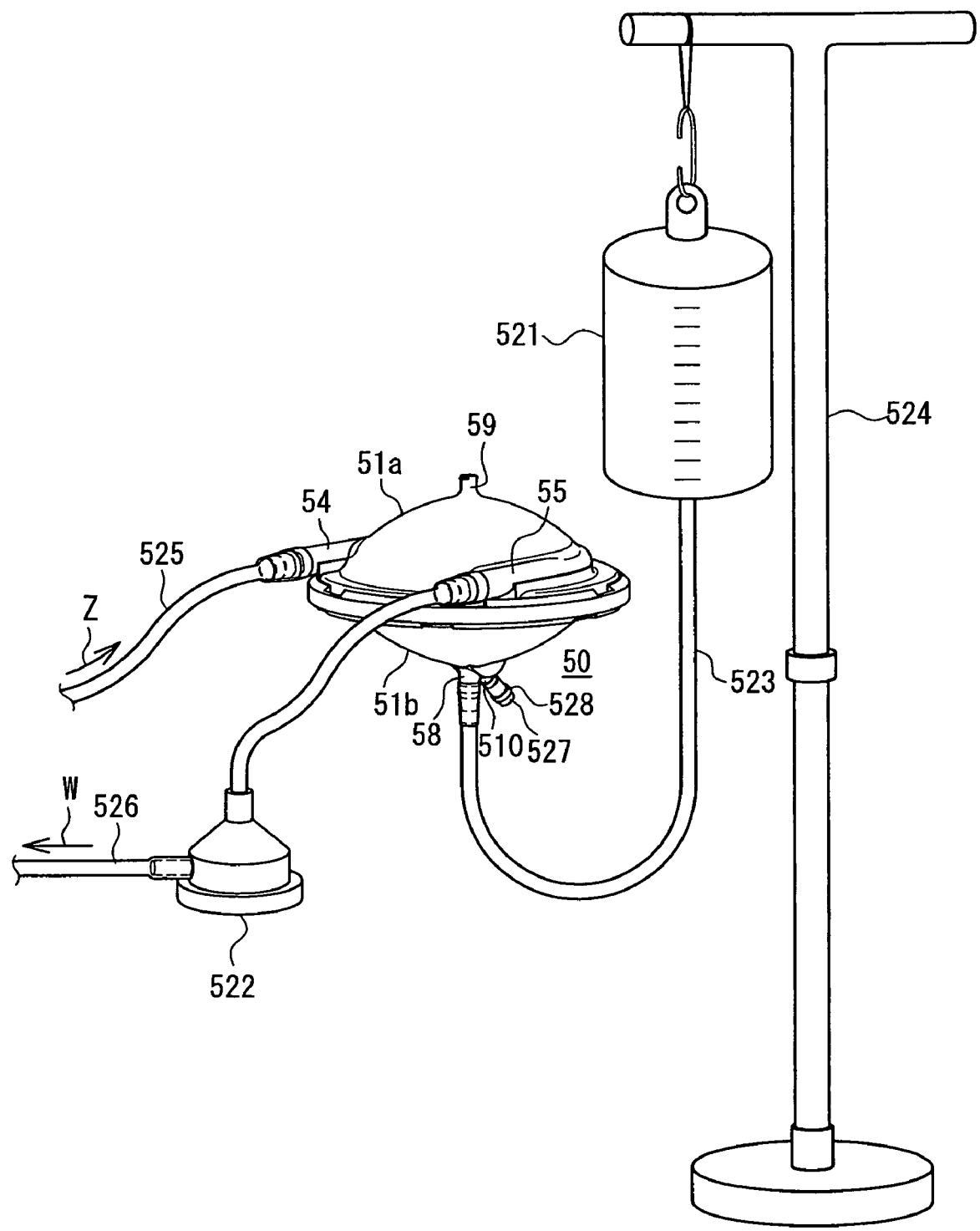
FIG. 21 is a perspective view showing an example of an extracorporeal blood circulation apparatus using the closed-type blood reservoir shown in FIG. 19.

The blood reservoir is for example used as shown in FIG. 21. FIG. 21 shows the configuration of an extracorporeal blood circulation apparatus that is constituted using a closed-type blood reservoir having the structure discussed above. This extracorporeal blood circulation apparatus is provided with a closed-type blood reservoir 50 with the above configuration, a volume adjustment liquid reservoir 521, and a blood pump 522 made from a centrifugal pump, for example. FIG. 21 shows the state during extracorporeal blood circulation, and the closed-type blood reservoir 50 is disposed such that the blood storage chamber shell 51a is above and the volume adjustment chamber shell 51b is below.

The volume adjustment liquid reservoir 521 is connected to the volume adjustment liquid port 58 of the closed-type blood reservoir 50 by a flexible adjustment liquid route tube 523, which is a conduit member. An air discharge tube 527 is connected to the volume adjustment chamber air discharge port 510, and is narrowed and closed off by forceps 528. The inlet of the blood pump 522 is connected to the blood outlet port 55 of the closed-type blood reservoir 50. The adjustment liquid reservoir 521 is supported by a support fitting 524 that allows its height relative to the closed-type blood reservoir 50 to be adjusted. A flexible blood-removal side tube 525 that is connected to the site where blood is withdrawn from the body is connected to the blood inlet port 54 of the closed-type blood reservoir 50, and blood flows in as shown by the arrow Z. A flexible blood-return side tube 526 that is connected to the site where blood is returned is connected to the ejection opening of the blood pump 522, and blood flows out as shown by the arrow W.

The adjustment liquid reservoir 521 has the function of storing the volume adjustment liquid that is injected to and ejected from the volume adjustment chamber 52 of the closed-type blood reservoir 50 (see FIG. 20). The adjustment liquid route tube 523 is for example constituted by a flexible tube, and by narrowing the tube with forceps it is possible to block, open, or partially block the flow route, allowing the flow route cross-sectional area to be changed. It is also possible to adopt a structure in which the adjustment liquid route tube 523 has a flow route adjustment member for changing the flow route cross-sectional area, such as a cock, within its flow route.

The adjustment liquid reservoir 521 has a measurement portion, such as a scale, for measuring the amount of volume adjustment liquid that is being stored.

By changing the position where the adjustment liquid reservoir 521 is supported by the support fitting 524 in order to adjust the height of the adjustment liquid reservoir 521 with respect to the site where blood is withdrawn from the body, that is, to adjust the level of the volume adjustment liquid, it is possible to increase or decrease the amount of volume adjustment liquid that is stored in the volume adjustment chamber 52. Thus, the volume of the blood storage chamber 51 is adjusted by moving the septum 53. As long as the volume of the volume adjustment chamber 52 is measured before staring blood storage, then from the change in its volume it is possible to know the amount of change in the volume of the blood storage chamber 51. The amount of change in the volume of the volume adjustment chamber 52 can be measured from the change in the amount of volume adjustment liquid that is accommodated by the adjustment liquid reservoir 521.

Figure 22:
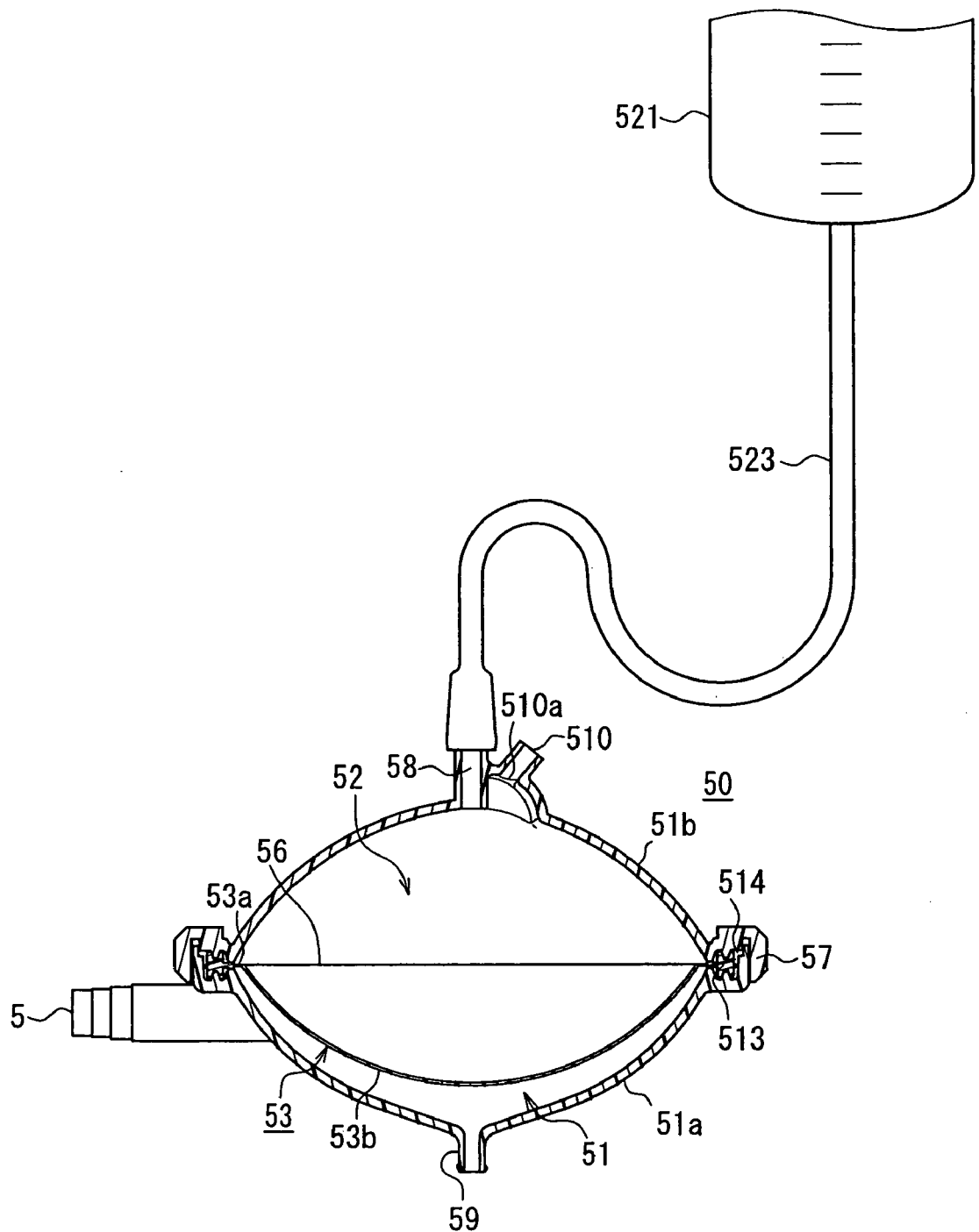
FIG. 22 is a cross-sectional diagram showing the state during priming of the extracorporeal blood circulation apparatus shown in FIG. 19.
Figure 23:
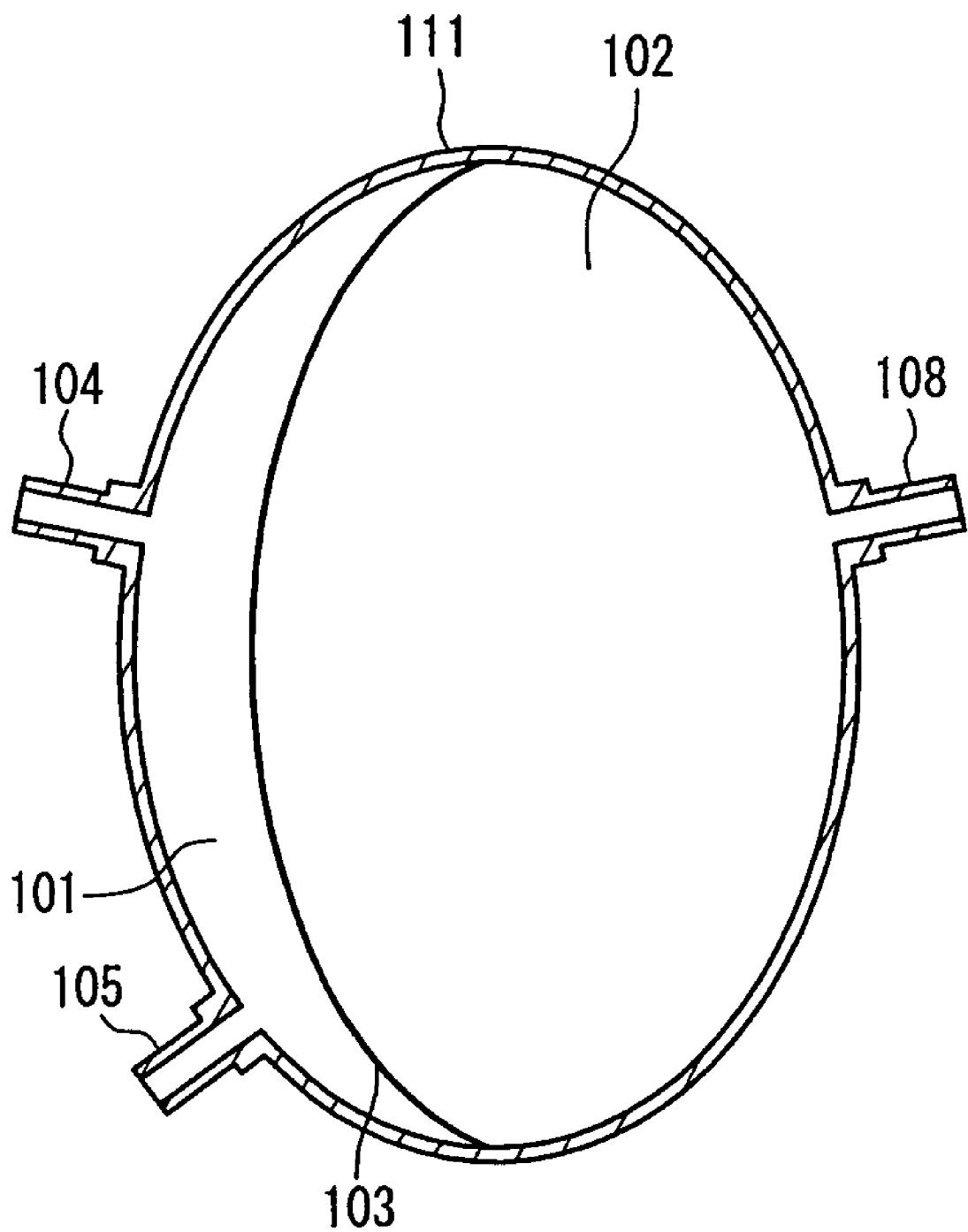
FIG. 23 is a cross-sectional diagram showing an example of a conventional closed-type blood reservoir.
Figure 24:
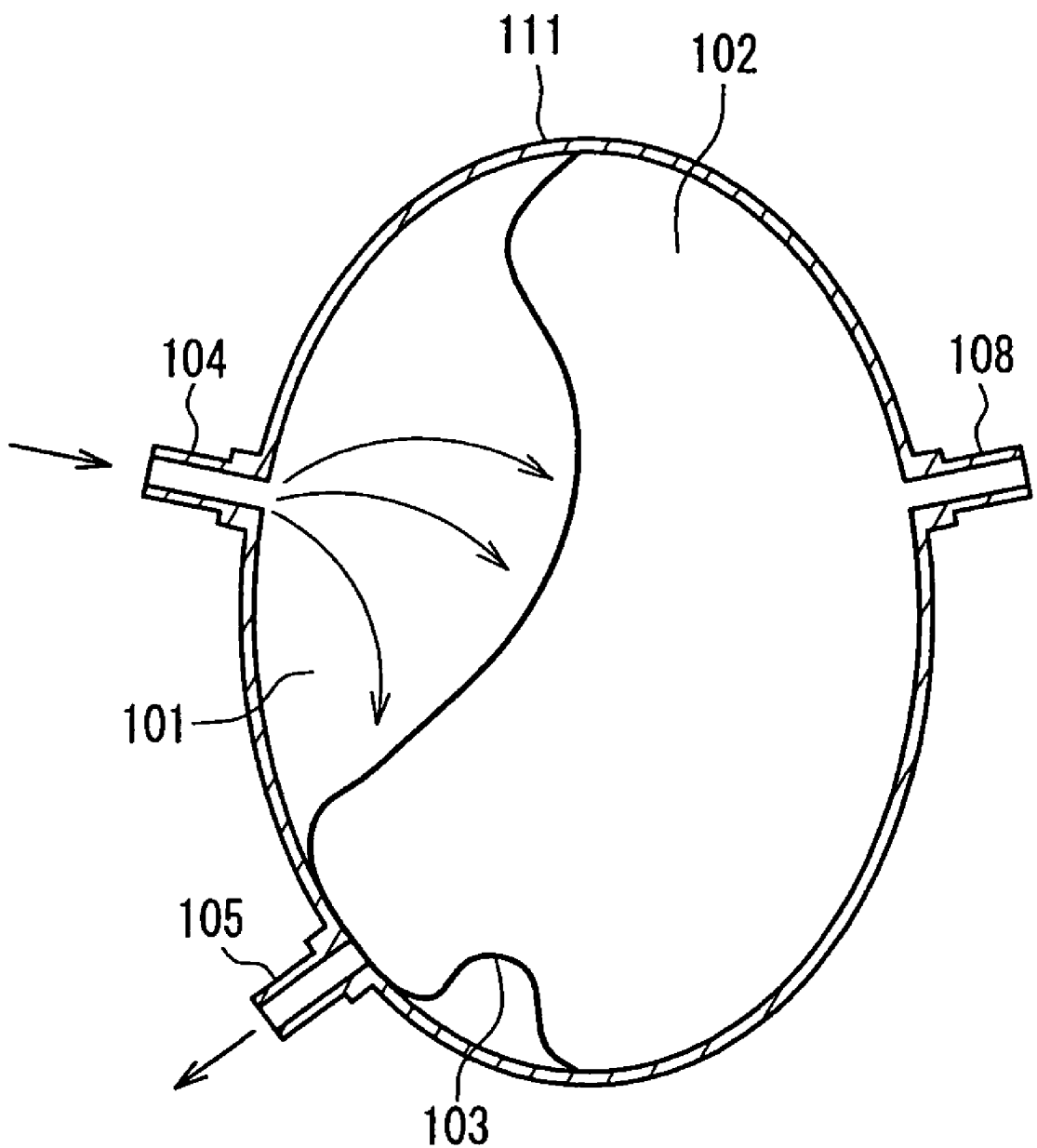
FIG. 24 is a cross-sectional diagram showing an example of a conventional closed-type blood reservoir.

The state of the closed-type blood reservoir 50 during the task of priming the extracorporeal blood circulation apparatus is shown in FIG. 22. Unlike the illustration in FIG. 21, the closed-type blood reservoir 50 is disposed such that the volume adjustment chamber shell 51b is above and the blood storage chamber shell 51a is below. Consequently, the volume adjustment liquid port 58 and the tip of the volume adjustment chamber air discharge port 510 point upwards. The volume adjustment chamber air discharge port 510 is open. Volume adjustment liquid (such as saline solution) is introduced into the volume adjustment chamber 52 from the adjustment liquid reservoir 521.

As discussed above, the volume adjustment chamber shell 51b has a shape in which its center portion comes to an apex, and the volume adjustment chamber air discharge port 510 is disposed in the center portion of the volume adjustment chamber shell 51b adjacent to the volume adjustment liquid port 58. Consequently, the volume adjustment chamber air discharge port 510 is kept at the highest point of the volume adjustment chamber 52. For this reason, as the saline solution is introduced, the buoyancy of the air that remains in the volume adjustment chamber 52 causes it to rise up and collect near the volume adjustment chamber air discharge port 510. The result is that air is discharged rapidly and the task of loading the priming liquid can be carried out efficiently.

Further, because the tip of the volume adjustment liquid port 58 is located farther from the wall face of the volume adjustment chamber shell 51b than the tip of the volume adjustment chamber air discharge port 510, during priming as shown in FIG. 22 the tip of the volume adjustment liquid port 58 is higher than the tip of the volume adjustment chamber air discharge port 510. Because the air discharge port opening 510a is disposed recessed outward from the inner wall surface of the volume adjustment chamber shell 51b, air that rises up easily enters the volume adjustment chamber air discharge port 510.

After priming is complete, the closed-type blood reservoir 50 is flipped over and returned to the state shown in FIG. 21. Then, when extracorporeal blood circulation is started, the blood that is withdrawn from the body is introduced into the blood storage chamber 51 through the blood inlet port 54, and is discharged from the blood storage chamber 51 through the blood outlet port 55. At this time, when the height of the volume adjustment liquid reservoir 521 is adjusted so that the saline solution of the volume adjustment chamber 52 is discharged into the volume adjustment liquid reservoir 521, the septum 53 moves in accordance with the amount of saline solution that has been discharged from the volume adjustment chamber 52, increasing the volume of the blood storage chamber 51. In other words, an amount of blood that corresponds to the amount of saline solution that has been transferred to the volume adjustment liquid reservoir 521 becomes stored in the blood storage chamber 51. That amount can be ascertained reliably from the volume adjustment liquid reservoir 521.

Conversely, when the position of the volume adjustment liquid reservoir 521 is raised in order to send the saline solution to the volume adjustment chamber 52, the septum 53 moves toward in the blood storage chamber 51 in accordance with that amount of saline solution and reduces the volume of the blood storage chamber 51. As a result, the blood that is stored in the blood storage chamber 51 is discharged from the blood reservoir and subsequently is returned to the body. That amount can be ascertained reliably by the volume adjustment liquid reservoir 521.

As illustrated above, the volume of the blood storage chamber 51 can be changed with ease, and, moreover, the volume of the changed blood storage chamber 51, that is, the blood storage volume, can be ascertained readily. Consequently, in extracorporeal blood circulation it is not necessary to select a blood reservoir with an appropriate volume based on patient conditions each time, and by preparing a blood reservoir with a certain degree of volume it is possible to handle small to large volumes.

It should be noted that the volume adjustment chamber 52 is isolated from the blood storage chamber 51 by the septum 53, and thus the blood will not become contaminated. Consequently, it is not necessary to specifically to use a sterilized adjustment liquid to serve as the adjustment liquid that is filled into the volume adjustment chamber 52, but it is desirable for a sterilized isotonic liquid such as saline solution to be used in case the septum 53 should break.

The materials forming the blood storage chamber shell 51a and the volume adjustment chamber shell 51b can be the same in the blood reservoir of Embodiment 1. The material for the septum 53 also can be the same as the material of the septum in the blood reservoir of Embodiment 1.

Working Example

Figure 15:
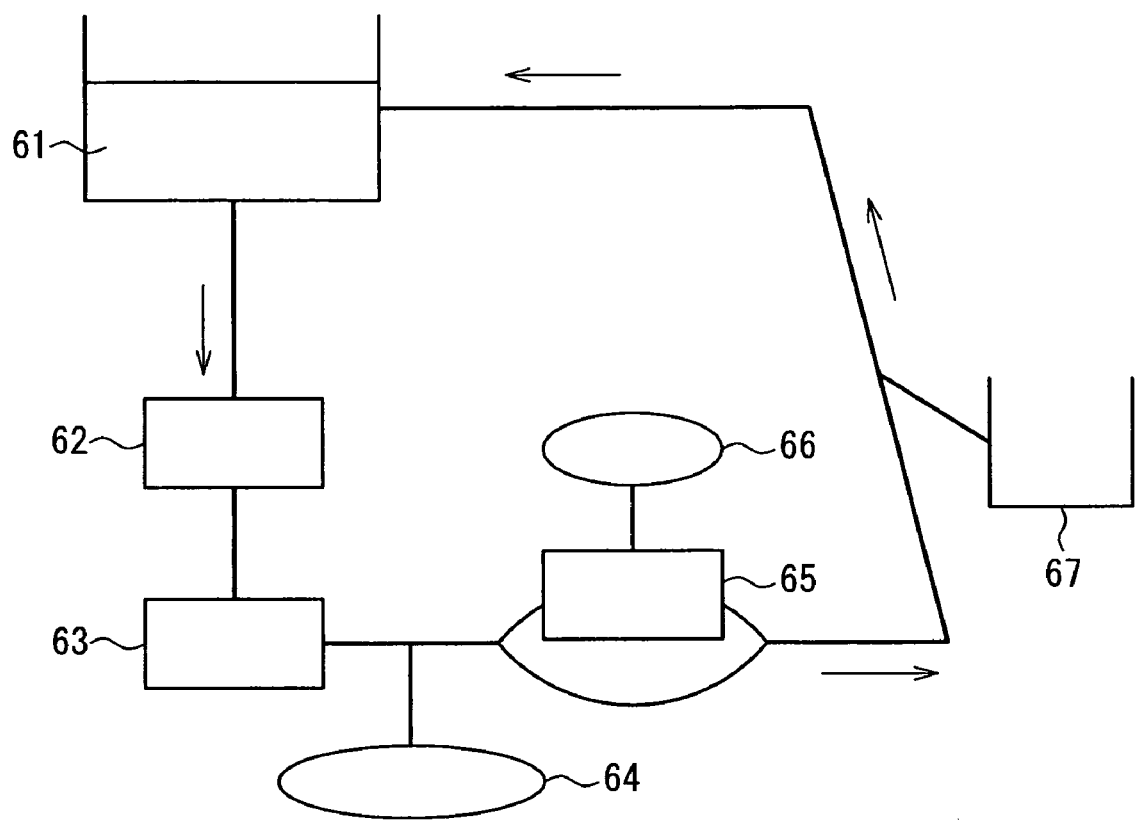
FIG. 15 is a schematic view of the test system that is used in the working example.

Using the system shown in FIG. 15, the time until air bubbles begin to flow out from the closed-type blood reservoir, and the amount of air that remains in the blood storage chamber when air bubbles begin to flow out from the closed-type blood reservoir, were measured. These measurements were performed with the blood storage volume set to a maximum, and set to a minimum.

In FIG. 15, reference number 61 denotes heparin-added bovine blood, 62 is a pump, 63 is a filter, 64 is an injector for effectively mixing in air bubbles, 65 is the closed-type blood reservoir A shown in FIG. 2 or the closed-type blood reservoir B shown in FIG. 6, 66 is a vessel for measuring the amount of air bubbles, and 67 is a vessel for recovering the priming liquid that has been filled into the blood storage chamber, for example, prior to the start of testing. It should be noted that difference between the closed-type blood reservoir A and the closed-type blood reservoir B is whether or not the first blood flow route 115 and the second blood flow route 114 are connected. The vessel 66 is attached to the closed-type blood reservoir 65 after circulation is over.

The amount of air that remains in the closed-type blood reservoir was measured as follows. First, the closed-type blood reservoir 65 was tilted to move the air remaining in the blood storage chamber away from the blood storage chamber air discharge port and fill the blood storage chamber air discharge port with the liquid within the blood storage chamber. Next, the vessel 66, filled with the liquid, was attached to the blood storage chamber air discharge port. At this time, care was given to keep air from entering the closed-type blood reservoir 65. Then, the closed-type blood reservoir was returned to its original orientation to move the air that remained within the blood storage chamber from the blood storage chamber to the vessel 66, and the amount of air was measured.

TABLE 1

| | flow rate (L/min) | | 2 | 3 | 4 |
|---|---|---|---|---|---|
| minimum blood storage amount | closed-type blood reservoir A | air amount (mL) | 10 | 6 | 0.8 |
| | | time (sec) | 64 | 45 | 6 |
| | closed-type blood reservoir B | air amount (mL) | 9 | 1.2 | 0.4 |
| | | time (sec) | 49 | 12 | 3 |
| maximum blood storage amount | closed-type blood reservoir A | air amount (mL) | 93 | 90 | 25 |
| | | time (sec) | 553 | 521 | 144 |
| | closed-type blood reservoir B | air amount (mL) | 80 | 68 | 3.2 |
| | | time (sec) | 492 | 399 | 22 |

It can be confirmed from Table 1 that the closed-type blood reservoir A, in which the first blood flow route 115 and the second blood flow route 114 are not connected (see FIG. 2), exhibited a longer time before air bubbles began to flow out from the closed-type blood reservoir, and more air remained in the blood storage chamber when air bubbles began to flow out from the closed-type blood reservoir, than the closed-type blood reservoir B, in which the first blood flow route 115 and the second blood flow route 114 are linked (see FIG. 6). This result indicates that the closed-type blood reservoir A has better ability to remove air bubbles and is safer than the closed-type blood reservoir B.

INDUSTRIAL APPLICABILITY

The first through third closed-type blood reservoirs of the invention are useful in the construction of an extracorporeal blood circulation system because the blood outlet port is kept from being blocked off by the septum for varying the volume of the blood storage chamber. The fourth closed-type blood reservoir of the invention is useful in the construction of an extracorporeal blood circulation system because it easily can be set to an orientation that facilitates the effective discharge of air from the volume adjustment chamber during priming.

The invention claimed is:

1. A closed-type blood reservoir comprising:
an outer shell in which a blood storage chamber shell and a volume adjustment chamber shell, each having a curved shape that is outwardly convex, are joined together and form a space therewithin;
a flexible septum that is interposed between the blood storage chamber shell and the volume adjustment chamber shell, and that divides the space into a blood storage chamber for storing blood and a volume adjustment chamber for storing volume adjustment liquid;
a blood inlet port, a blood outlet port, and a blood storage chamber air discharge port, that are provided in the blood storage chamber shell such that they are in communication with the blood storage chamber; and
a volume adjustment liquid port provided in the volume adjustment chamber shell such that it is in communication with the volume adjustment chamber, for injecting and ejecting the volume adjustment liquid to and from the volume adjustment chamber;
wherein the blood inlet port and the blood outlet port each are provided tangentially to the inner surface of the blood storage chamber shell such that blood that flows into the blood storage chamber from the blood inlet port can swirl along the inner surface of the blood storage chamber shell; and
wherein the closed-type blood reservoir has a first blood flow route, provided in the blood storage chamber, that is formed by an outward concavity of the inner surface of the blood storage chamber shell, and that is in communication with the blood outlet port and at least part of which is formed in the direction of extension of the blood outlet port.

2. The closed-type blood reservoir according to claim 1, wherein the closed-type blood reservoir has a second blood flow route, provided in the blood storage chamber, that is formed by an outward concavity of the inner surface of the blood storage chamber shell, and that is in communication with the blood inlet port and at least part of which is formed in the direction of extension of the blood inlet port.

3. The closed-type blood reservoir according to claim 2, wherein the first blood flow route and the second blood flow route are connected to one another, and form a single continuous blood flow route.

4. The closed-type blood reservoir according to claim 2, wherein the blood inlet port and the blood outlet port open in the same direction and are provided in the blood storage chamber shell such that their center axes are parallel.

5. The closed-type blood reservoir according to claim 2, wherein a portion of the inner surface of the blood storage chamber shell that is located between the first blood flow route and the second blood flow route in the circumferential direction forms part of a continuous curved surface from the circumferential edge portion of the inner surface toward its center portion.

6. An extracorporeal blood circulation apparatus, comprising:
the closed-type blood reservoir according to claim 1;
an adjustment liquid reservoir for storing the volume adjustment liquid that is injected into and ejected from the volume adjustment chamber;
a conduit member that is connected to the volume adjustment liquid port and the volume adjustment liquid reservoir and that allows the flow rate to be adjusted; and
a blood pump that is connected to the blood outlet port.

7. A closed-type blood reservoir comprising:
an outer shell in which a blood storage chamber shell and a volume adjustment chamber shell each having a curved shape that is outwardly convex are joined together and form a space therewithin;
a flexible septum that is interposed between the blood storage chamber shell and the volume adjustment chamber shell, and that divides the space into a blood storage chamber for storing blood and a volume adjustment chamber for storing volume adjustment liquid;
a blood inlet port, a blood outlet port, and a blood storage chamber air discharge port, that are provided in the blood storage chamber shell; and
a volume adjustment liquid port for injecting and ejecting the volume adjustment liquid and a volume adjustment chamber air discharge port that are provided in the volume adjustment chamber shell;
wherein part of the inner circumferential portion region of the septum along the outer circumferential edge of the blood storage chamber shell forms a flat portion that is substantially flat, and the inner region of the flat portion is molded such that it can project as a curved surface toward the blood storage chamber shell or the volume adjustment chamber shell.

8. A closed-type blood reservoir comprising:
an outer shell in which a blood storage chamber shell and a volume adjustment chamber shell, each having a curved shape that is outwardly convex, are joined together and form a space therewithin;
a flexible septum that is interposed between the blood storage chamber shell and the volume adjustment chamber shell, and that divides the space into a blood storage chamber for storing blood and a volume adjustment chamber for storing volume adjustment liquid;
a blood inlet port, a blood outlet port, and a blood storage chamber air discharge port, that are provided in the blood storage chamber shell; and
a volume adjustment liquid port for injecting and ejecting the volume adjustment liquid and a volume adjustment chamber air discharge port that are provided in the volume adjustment chamber shell;
wherein the inner surface of the blood storage chamber shell has a shape of a rotated circular arc surface; and
wherein the septum is a molded portion that is molded such that at least its central region can project as a curved surface toward the blood storage chamber shell or the volume adjustment chamber shell, and the curvature of the molded shape of the molded portion is smaller than the curvature of the blood storage chamber shell inner surface.

9. The closed-type blood reservoir according to claim 8, wherein part of the region of the circumferential portion of the septum along the inner side of an outer circumferential edge of the blood storage chamber shell forms a flat portion that is substantially flat.

10. An extracorporeal blood circulation apparatus, comprising:
the closed-type blood reservoir according to claim 7;
an adjustment liquid reservoir for storing the volume adjustment liquid that is injected into and ejected from the volume adjustment chamber;
a conduit member that is connected to the volume adjustment liquid port and the volume adjustment liquid reservoir and that allows the flow rate to be adjusted; and
a blood pump that is connected to the blood outlet port.

11. An extracorporeal blood circulation apparatus, comprising:
the closed-type blood reservoir according to claim 8;
an adjustment liquid reservoir for storing the volume adjustment liquid that is injected into and ejected from the volume adjustment chamber;
a conduit member that is connected to the volume adjustment liquid port and the volume adjustment liquid reservoir and that allows the flow rate to be adjusted; and
a blood pump that is connected to the blood outlet port.

12. A closed-type blood reservoir comprising:
an outer shell in which a blood storage chamber shell and a volume adjustment chamber shell that are outwardly convex are joined together and form a space therewithin;
a flexible septum that is interposed between the blood storage chamber shell and the volume adjustment chamber shell, and that divides the space into a blood storage chamber for storing blood and a volume adjustment chamber for storing volume adjustment liquid;
a blood inlet port, a blood outlet port, and a blood storage chamber air discharge port, that are provided in the blood storage chamber shell; and
a volume adjustment liquid port for injecting and ejecting the volume adjustment liquid and a volume adjustment chamber air discharge port that are provided in the volume adjustment chamber shell; wherein the volume adjustment chamber shell has a shape in which its center portion is an apex; and wherein the volume adjustment liquid port is provided in the center portion of the volume adjustment chamber shell and the volume adjustment chamber air discharge port is provided adjacent to the volume adjustment liquid port.

13. The closed-type blood reservoir according to claim 12, wherein an air discharge port opening that is formed in the volume adjustment chamber shell by providing the volume adjustment chamber air discharge port is disposed within a concavity that is provided in the volume adjustment chamber shell from its inner wall surface toward the outside.

14. An extracorporeal blood circulation apparatus, comprising:

the closed-type blood reservoir according to claim 12;

an adjustment liquid reservoir for storing the volume adjustment liquid that is injected into and ejected from the volume adjustment chamber;

a conduit member that is connected to the volume adjustment liquid port and the volume adjustment liquid reservoir and that allows the flow rate to be adjusted; and a blood pump that is connected to the blood outlet port.

* * * * *